(12) United States Patent
Vigh et al.

(10) Patent No.: US 6,923,896 B2
(45) Date of Patent: Aug. 2, 2005

(54) ELECTROPHORESIS APPARATUS AND METHOD

(75) Inventors: Gyula Vigh, Magnolia, TX (US); David Ogle, Cowan (AU); Dennis Brian Rylatt, Ryde (AU)

(73) Assignees: The Texas A&M University System, College Station, TX (US); Gradipore Limited, Frenchs Forest (AU)

(*) Notice: Subject to any disclaimer, the term of this patent is extended or adjusted under 35 U.S.C. 154(b) by 59 days.

(21) Appl. No.: 09/961,591

(22) Filed: Sep. 22, 2001

(65) Prior Publication Data

US 2002/0043465 A1 Apr. 18, 2002

(30) Foreign Application Priority Data

Sep. 22, 2000 (AU) .............................................. PR0313
Dec. 22, 2000 (AU) .............................................. PR2299

(51) Int. Cl.[7] ..................... G01N 27/447; G01N 27/453
(52) U.S. Cl. ...................................... 204/548; 204/644
(58) Field of Search ................................ 204/450, 459, 204/548, 600, 610, 644

(56) References Cited

U.S. PATENT DOCUMENTS

| | | |
|---|---|---|
| 3,878,564 A | 4/1975 | Yao et al. |
| 3,989,613 A | 11/1976 | Gritzner |
| 4,036,748 A | 7/1977 | Knickel et al. |
| 4,045,337 A | 8/1977 | Knickel et al. |
| 4,045,455 A | 8/1977 | Vogel |
| 4,069,215 A | 1/1978 | Elfert et al. |
| 4,115,225 A | 9/1978 | Parsi |
| 4,123,342 A | 10/1978 | Ahlgren |
| 4,174,439 A | 11/1979 | Rauenbusch et al. |
| 4,196,304 A | 4/1980 | Naumann |
| 4,204,929 A | 5/1980 | Bier |
| 4,217,227 A | 8/1980 | Elfert et al. |
| 4,238,306 A | 12/1980 | Perry et al. |
| 4,238,307 A | 12/1980 | Perry et al. |
| 4,243,507 A * | 1/1981 | Martin et al. ................ 204/610 |

(Continued)

FOREIGN PATENT DOCUMENTS

| | | |
|---|---|---|
| EP | 0 369 945 A2 | 5/1990 |
| WO | WO 97/14486 | 4/1997 |
| WO | WO 98/21384 | 5/1998 |
| WO | WO 98/43718 | 10/1998 |

*Primary Examiner*—Kaj K. Olsen
(74) *Attorney, Agent, or Firm*—Morgan Lewis & Bockius LLP

(57) ABSTRACT

An electrophoretic apparatus comprising: a first electrolyte chamber containing a first electrode; a second electrolyte chamber containing a second electrode; a first sample chamber disposed between the first and second electrolyte chambers and proximate to the first electrolyte chamber; a second sample chamber disposed between the first sample chamber and the second electrolyte; three ion-permeable barriers separating the first electrolyte chamber, the first sample chamber, the second sample chamber, and the second electrolyte chamber, respectively, wherein the ion-permeable barriers impede convective mixing of the contents in each of the respective chambers; a first electrolyte reservoir and a second electrolyte reservoir in fluid communication with the first and second electrolyte chambers, respectively; a first sample reservoir and a second sample reservoir in fluid communication with the first and second sample chambers, respectively; means adapted for communicating a first electrolyte and a second electrolyte between the respective electrolyte chambers and reservoirs; means adapted for communicating a first fluid and a second fluid between the respective sample chambers and reservoirs, wherein at least one of the first and second fluid contains at least a sample, wherein application of an electric potential causes migration of at least one component through at least one of the ion-permeable barriers.

28 Claims, 12 Drawing Sheets

U.S. PATENT DOCUMENTS

| | | | |
|---|---|---|---|
| 4,252,652 A | 2/1981 | Elfert et al. |
| 4,259,079 A | 3/1981 | Blum |
| 4,269,967 A | 5/1981 | Elfert et al. |
| 4,276,140 A | 6/1981 | Jain |
| 4,279,724 A | 7/1981 | Hearn et al. |
| 4,299,677 A | 11/1981 | Venkatasubramanian et al. |
| 4,322,275 A | 3/1982 | Jain |
| 4,362,612 A | 12/1982 | Bier |
| 4,376,023 A | 3/1983 | Venkatsubramanian et al. |
| 4,381,232 A | 4/1983 | Brown |
| 4,383,923 A | 5/1983 | Elfert |
| 4,396,477 A | 8/1983 | Jain |
| 4,441,978 A | 4/1984 | Jain |
| 4,533,447 A | 8/1985 | Meldon |
| 4,608,140 A | 8/1986 | Goldstein |
| 4,661,224 A | 4/1987 | Goldstein et al. |
| 4,673,483 A | 6/1987 | Mandle |
| 4,711,722 A | 12/1987 | Toyoshi et al. |
| 4,746,647 A | 5/1988 | Svenson |
| 4,780,411 A | 10/1988 | Piejko et al. |
| 4,897,169 A | 1/1990 | Bier et al. |
| 4,963,236 A | 10/1990 | Rodkey et al. |
| 5,039,386 A | 8/1991 | Margolis |
| 5,043,048 A | 8/1991 | Muralidhara |
| 5,080,770 A | 1/1992 | Culkin |
| 5,082,548 A | 1/1992 | Faupel et al. |
| 5,087,338 A | 2/1992 | Perry et al. |
| 5,096,547 A | 3/1992 | Klotz et al. |
| 5,114,555 A | 5/1992 | Stimpson |
| 5,127,999 A | 7/1992 | Klotz et al. |
| 5,160,594 A | 11/1992 | Huff et al. |
| 5,173,164 A | 12/1992 | Egen et al. |
| 5,185,086 A | 2/1993 | Kaali et al. |
| 5,238,570 A | 8/1993 | Hugl et al. |
| 5,277,774 A | 1/1994 | Shmidt et al. |
| 5,336,387 A | 8/1994 | Egen et al. |
| 5,340,449 A | 8/1994 | Shukla |
| 5,352,343 A | 10/1994 | Bailes et al. |
| 5,407,553 A | 4/1995 | Herron et al. |
| 5,420,047 A | 5/1995 | Brandt et al. |
| 5,437,774 A | 8/1995 | Lautsen |
| 5,441,646 A | 8/1995 | Heller et al. |
| 5,490,939 A | 2/1996 | Gerigk et al. |
| 5,503,744 A | 4/1996 | Ikematsu et al. |
| 5,504,239 A | 4/1996 | Mehl et al. |
| 5,558,753 A | 9/1996 | Gallagher et al. |
| 5,561,115 A | 10/1996 | Tenold |
| 5,565,102 A | 10/1996 | Brandt et al. |
| 5,610,285 A | 3/1997 | Lebing et al. |
| 5,662,813 A | 9/1997 | Sammons et al. |
| 5,723,031 A | 3/1998 | Durr et al. |
| 5,733,442 A | 3/1998 | Shukla |
| 5,736,023 A | 4/1998 | Gallagher et al. |
| 5,868,938 A | 2/1999 | Bomer et al. |
| 5,891,736 A | 4/1999 | Chapoteau et al. |
| 5,906,724 A | 5/1999 | Sammons et al. |
| 5,938,904 A | 8/1999 | Bader et al. |
| 5,986,075 A | 11/1999 | DuBose et al. |
| 6,093,296 A | 7/2000 | Soane et al. |
| 6,117,297 A | 9/2000 | Goldstein |
| 6,129,842 A | 10/2000 | Kostanian |
| 6,171,825 B1 | 1/2001 | Chan et al. |

\* cited by examiner

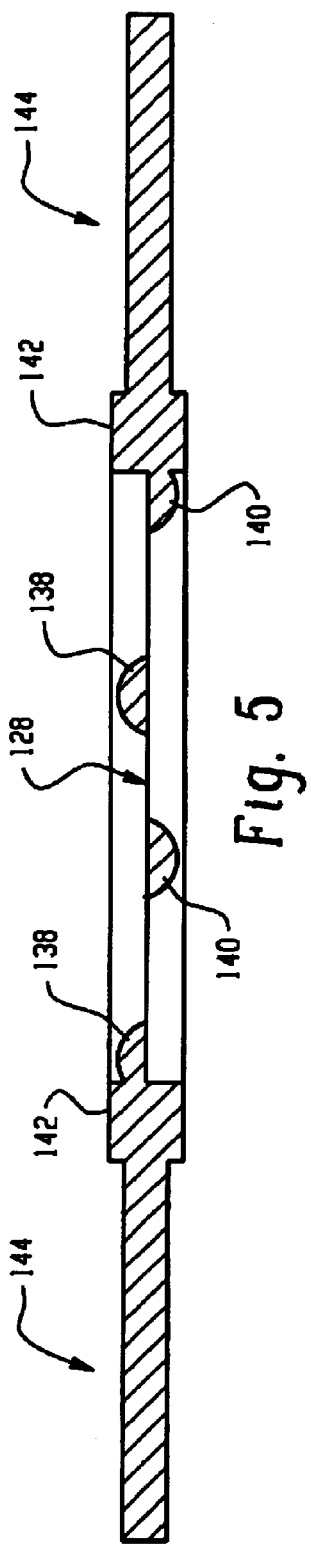
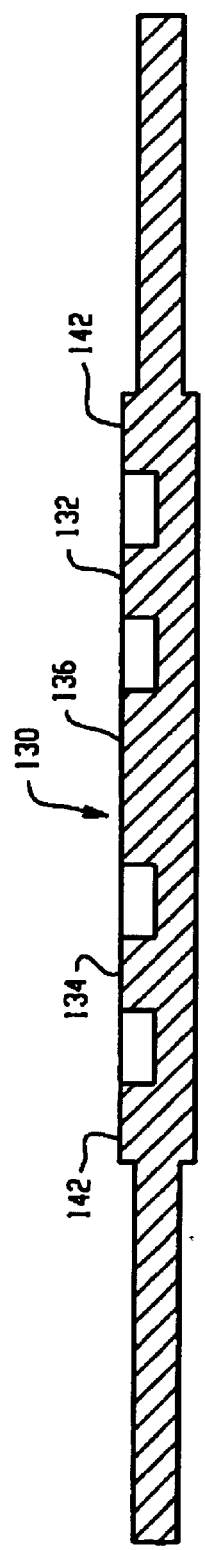
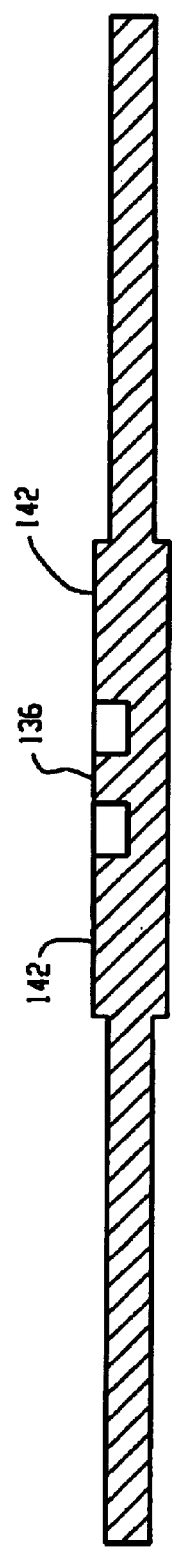

ELECTROPHORESIS APPARATUS AND METHOD

BACKGROUND OF THE INVENTION

The present invention relates to an electrophoresis apparatus and method suitable for electrophoretically altering the original composition of a mixture that contains at least one ampholytic component.

When ampholytic compounds, such as amino acids, peptides, oligopeptides, proteins, and the like are present in a solution at a low concentration, their charge-state depends on the pH of their environment. At a certain characteristic pH value, the net charge—and consequently, the electrophoretic mobility—of an ampholytic compound becomes zero. That pH value is called the pI value of the ampholytic compound. When two ampholytic compounds have different pI values, their net charge becomes zero at different pH values. Thus, if a pH gradient is established in an electric field, the two ampholytic species achieve zero net charge at different points of the pH gradient that can result in their separation. Such separations are called isoelectric focusing (IEF) separations. IEF separations have been achieved in (i) artificial pH gradients created from non-amphoteric buffers either at constant or spatially varying temperatures, (ii) natural pH gradients created from carrier ampholytes or from the very components of the mixture to be separated (autofocusing), and (iii) immobilized pH gradients.

IEF separations typically rely on anti-convective means to preserve the stability of the pH gradient. The IEF principle has been utilized for both analytical and preparative-scale separation of both simple and complex mixtures of ampholytic components. IEF separations have been obtained in thin-layer format, column-format and in multi-compartment format, in both static and flowing media. In flowing media, separations have been achieved in both straight-through and recycling format. IEF separations often take considerable time because the electrophoretic mobility of each ampholytic species becomes low as they approach the point in the pH gradient where they become isoelectric.

Therefore, there is a need for IEF separation schemes and equipment which (i) minimize the distance the components have to migrate electrophoretically to achieve separation, (ii) maximize the electric field strength that brings about the electrophoretic separation without causing detrimental heating effects, (iii) maximize the production rate that can be achieved in unit separation space and time, and (iv) minimize the use of auxiliary agents needed for the electrophoretic separation.

The present invention provides an apparatus and method which can electrophoretically alter the original composition of a mixture that contains at least one ampholytic component.

SUMMARY OF THE INVENTION

In accordance with the present invention, there is provided an electrophoresis apparatus and method which can electrophoretically alter the original composition of a mixture that contains at least one ampholytic component.

Further, in accordance with the present invention, there is provided an electrophoresis apparatus and system which (i) minimizes the distance the components have to migrate electrophoretically to achieve separation, (ii) maximizes the electric field strength that brings about the electrophoretic separation without causing detrimental heating effects, (iii) maximizes the production rate that can be achieved in unit separation space and time, and (iv) minimizes the use of auxiliary agents needed for the electrophoretic separation.

Still further, in accordance with the present invention, there is provided an electrophoretic apparatus comprising:

a first electrolyte chamber containing a first electrode;

a second electrolyte chamber containing a second electrode, wherein the second electrolyte chamber is disposed relative to the first electrolyte chamber so that the electrodes are adapted to generate an electric field in an electric field area upon application of a selected electric potential between the electrodes;

a first sample chamber disposed between the first and second electrolyte chambers and proximate to the first electrolyte chamber so as to be at least partially disposed in the electric field area;

a second sample chamber disposed between the first sample chamber and the second electrolyte chamber so as to be at least partially disposed in the electric field area;

a first ion-permeable barrier separating the first and second sample chambers so as to impede convective mixing of the contents in each of the first and second sample chambers;

a second ion-permeable barrier separating the first electrolyte chamber and the first sample chamber so as to impede convective mixing of the contents in each of the first sample chamber and the first electrolyte chamber;

a third ion-permeable barrier separating the second electrolyte chamber and the second sample chamber so as to impede convective mixing of the contents in each of the second sample chamber and the second electrolyte chamber;

a first electrolyte reservoir and a second electrolyte reservoir in fluid communication with the first and second electrolyte chambers, respectively;

a first sample reservoir and a second sample reservoir in fluid communication with the first and second sample chambers, respectively;

means adapted for communicating an associated first electrolyte between the first electrolyte chamber and the first electrolyte reservoir;

means adapted for communicating an associated second electrolyte between the second electrolyte chamber and the second electrolyte reservoir;

means adapted for communicating a first fluid between the first sample chamber and the first sample reservoir; and means adapted for communicating a second fluid between the second sample chamber and the second sample reservoir, wherein at least one of the first and second fluid contains at least a sample, wherein application of the selected electric potential causes migration of at least one component through at least one of the ion-permeable barriers.

In one preferred form, the first ion-permeable barrier is a membrane having a characteristic average pore size and pore size distribution. In one form, all the ion-permeable barriers are membranes having a characteristic average pore size and pore size distribution. This configuration of the apparatus is suitable for separating compounds on the basis of charge and or size.

In another preferred form, the first ion-permeable barrier is an isoelectric membrane having a characteristic pI value.

Preferably, the isoelectric membrane has a pI value in a range of about 2 to about 12.

In another preferred form, the second and third ion-permeable barriers are membranes having a characteristic average pore size and pore-size distribution.

In another preferred form, at least one of the second or third ion-permeable barriers is an isoelectric membrane having a characteristic pI value. Preferably, the at least one isoelectric membrane has a pI value in a range of about 2 to about 12. In another preferred form, both the second and third ion-permeable barriers are isoelectric membranes each having a characteristic pI value. Preferably, the isoelectric membranes have a pI value in a range of about 2 to about 12. When both the second and third ion-permeable barriers are isoelectric membranes, the membranes can have the same or different characteristic pI values.

The isoelectric membranes are preferably polyacrylamide-based membranes. It will be appreciated, however, that other isoelectric membranes would also be suitable for the present invention.

In another preferred form, the apparatus further comprises means for circulating electrolyte from each of the first and second electrolyte reservoirs through the respective first and second electrolyte chambers forming first and second electrolyte streams in the respective electrolyte chambers; and means for circulating contents from each of the first and second sample reservoirs through the respective first and second sample chambers forming first and second sample streams in the respective sample chambers.

Preferably, means for circulating the electrolyte and sample streams are pump arrangements separately controllable for independent movement of the electrolyte streams and the sample streams.

The apparatus may further include means for removing and replacing sample in the first or second sample reservoirs. The apparatus may also further include means to maintain temperature of electrolyte and sample solutions.

In another preferred form, the separation unit is provided as a cartridge or cassette fluidly connected to the electrolyte reservoirs and the sample reservoirs. In one preferred form, the separation unit is provided as a cartridge or cassette connected to the electrolyte reservoirs and the sample reservoirs.

Still further, in accordance with the present invention, there is provided a method for selectively removing at least one component from a selected sample comprising:

communicating a first electrolyte to a first electrolyte chamber containing a first electrode wherein the first electrolyte chamber is in fluid communication with a first electrolyte reservoir;

communicating a second electrolyte to a second electrolyte chamber containing a second electrode, wherein the second electrolyte chamber is disposed opposite the first electrolyte chamber and wherein the second electrolyte chamber is in fluid communication with a second electrolyte reservoir;

communicating a first fluid to a first sample chamber disposed between the first and second electrolyte chambers and proximate to the first electrolyte chamber, wherein the first sample chamber is in fluid communication with a first sample reservoir;

communicating a second fluid to a second sample chamber disposed between the first sample chamber and the second electrolyte chamber, wherein the second sample chamber is in fluid communication with a second sample reservoir, wherein a first ion-permeable barrier separates the first and second sample chambers, a second ion-permeable barrier separates the first electrolyte chamber and the first sample chamber, and a third ion-permeable barrier separates the second sample chamber and the second electrolyte chamber, wherein the ion-permeable barriers impede convective mixing between the respective chambers, wherein at least one of the first and second fluids contains at least a sample; and applying a selected electric potential to cause migration of at least one selected component through at least one of the ion-permeable barriers. Preferably, at least one sample component has a pI value.

In a preferred form, electrolyte from at least one of the first and second electrolyte reservoirs is circulated through the first or second electrolyte chamber forming a first or second electrolyte stream.

The choice of electrolyte in the first and second electrolyte chambers will depend on the compound or compounds to be treated, separated or transferred from a sample chamber to the other sample chamber, or one or both of the electrolyte chambers. Similarly, the choice of the pI of the isoelectric membranes will also depend on the compound or compounds to be treated, separated or transferred from a given sample.

Electrolytes such as acetic acid as the anolyte, and triethanol amine as the catholyte, have been found to be suitable for the separation of a number of components from biological samples. Salt such as NaCl may also be added to the electrolyte to assist. It will be appreciated, however, that other electrolytes would also be applicable, depending on the desired separation or treatment.

In another preferred form, electrolyte from both the first and second electrolyte reservoirs is circulated through the first and second electrolyte chambers forming first and second electrolyte streams.

In another preferred form, the contents of the first or second sample reservoir is circulated through the first or second sample chamber forming a first or second sample stream through the first or second sample chamber. In another preferred form, sample or liquid in the first or second sample reservoir is removed and replaced with fresh sample or liquid.

Preferably, substantially all transbarrier migration occurs upon the application of the electric potential. In another preferred form, the application of the electric potential is maintained until at least one desired component reaches a desired purity in at least one of the first and second sample chamber or in the first or second sample reservoirs.

Still further, in accordance with the present invention, there is provided an electrophoretic separation unit comprising:

a first electrolyte chamber containing a first electrode;

a second electrolyte chamber containing a second electrode, wherein the second electrolyte chamber is disposed relative to the first electrolyte chamber so that the electrodes are adapted to generate an electric field in an electric field area upon application of a selected electric potential between the electrodes;

a first sample chamber disposed between the first and second electrolyte chambers and proximate to the first electrolyte chamber so as to be at least partially disposed in the electric field area;

a second sample chamber disposed between the first sample chamber and the second electrolyte chamber so as to be at least partially disposed in the electric field area;

an isoelectric barrier separating the first and second sample chambers so as to impede convective mixing of the contents in each of the first and second sample chambers;

a first ion-permeable barrier separating the first electrolyte chamber and the first sample chamber so as to impede convective mixing of the contents in each of the first sample chamber and the first electrolyte chamber;

a second ion-permeable barrier separating the second electrolyte chamber and the second sample chamber so as to impede convective mixing of the contents in each of the second sample chamber and second electrolyte chamber;

means adapted for communicating an associated first electrolyte to the first electrolyte chamber;

means adapted for communicating an associated second electrolyte to the second electrolyte chamber;

means adapted for communicating a first fluid to the first sample chamber; and means adapted for communicating a second fluid to the second sample chamber, wherein at least one of the first and second fluids contains at least a sample;

wherein application of the selected electric potential causes migration of at least one component through at least one of the ion-permeable barriers.

Still further, in accordance with the present invention, there is provided a method for selectively altering the concentration of a selected sample:

communicating a first electrolyte to a first electrolyte chamber containing a first electrode;

communicating a second electrolyte to a second electrolyte chamber containing a second electrode;

communicating a first fluid to a first sample chamber disposed between the first and second electrolyte chambers and proximate to the first electrolyte chamber;

communicating a second fluid to a second sample chamber disposed between the first sample chamber and the second electrolyte chamber, wherein an isoelectric barrier separates the first and second sample chambers, a first ion-permeable barrier separates the first electrolyte chamber and the first sample chamber, and a second ion-permeable barrier separates the second sample chamber and the second electrolyte chamber, wherein the barriers impede convective mixing between the respective chambers, wherein at least one of the first and second fluids contains a sample; and applying a selected electric potential to cause migration of at least one selected component through at least one of the barriers.

An advantage of the present invention is that the apparatus and method have scale-up capabilities, increased separation speed, lower cost of operation, lower power requirements, and increased ease of use.

Yet another advantage of the present invention is that the apparatus and method have improved yields of the separated component, and improved purity of the separated component.

These and other advantages will be apparent to one skilled in the art upon reading and understanding the specification.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia before the priority date of each claim of this application.

BRIEF DESCRIPTION OF THE DRAWINGS

FIG. 5 is a cross-sectional view on the lines X—X of FIG. 4A.

FIG. 6 is a cross-sectional view on the lines XI—XI of FIG. 4A.

FIG. 7 is a cross-sectional view on the lines XII—XII of FIG. 4A.

DETAILED DESCRIPTION OF THE INVENTION

Before describing the preferred embodiments in detail, the principal of operation of the apparatus will first be described. An electric field or potential applied to ions in solution will cause the ions to move toward one of the electrodes. If the ion has a positive charge, it will move toward the negative electrode (cathode). Conversely, a negatively-charged ion will move toward the positive electrode (anode).

In the apparatus of the present invention, ion-permeable barriers that substantially prevent convective mixing between the adjacent chambers of the apparatus or unit are placed in an electric field and components of the sample are selectively transported through the barriers. The particular ion-permeable barriers used will vary for different applications and generally have characteristic average pore sizes and pore size distributions and/or isoelectric points allowing or substantially preventing passage of different components.

Having outlined some of the principles of operation of an apparatus in accordance with the present invention, an apparatus itself will be described.

Figure 1:
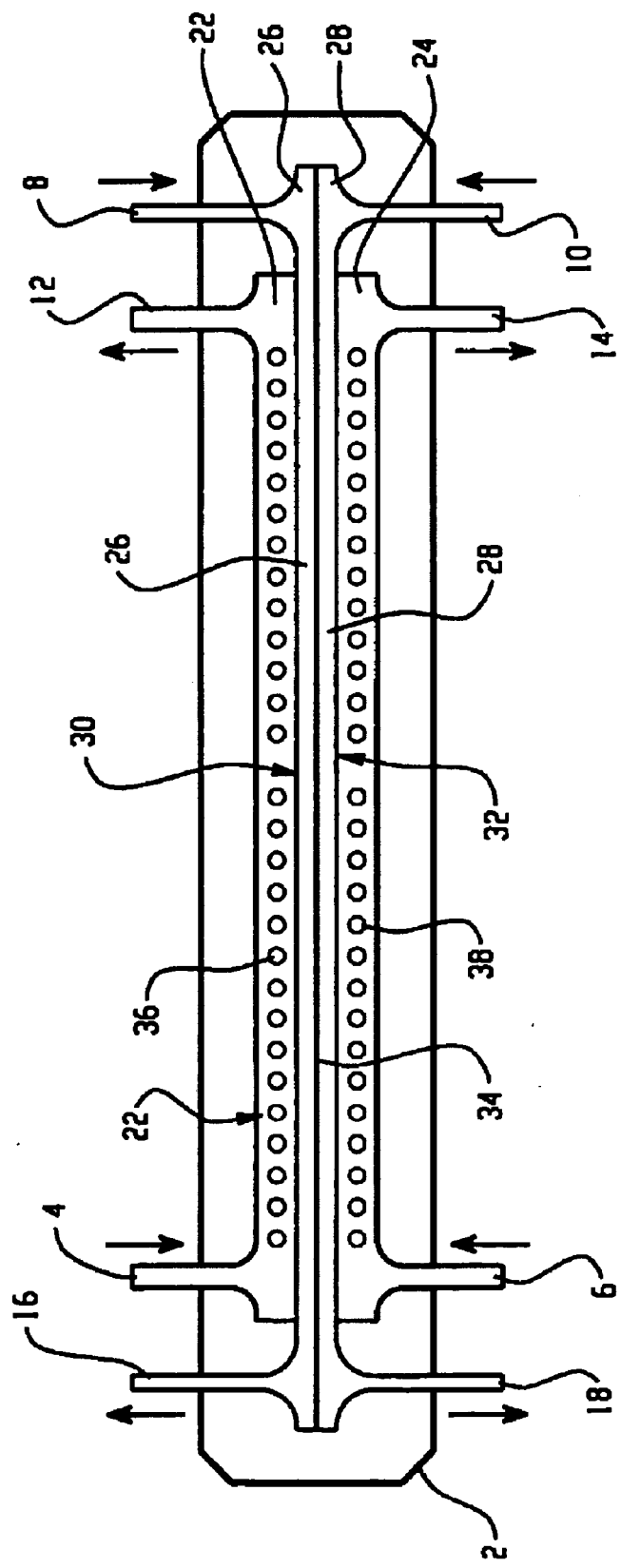
FIG. 1 is a schematic diagram of a separation unit for use in the present invention.

Referring to FIG. 1, a schematic representation of separation unit 2 is shown for the purpose of illustrating the general functionality of a separation device utilizing the technology of the present invention. Separation unit 2 comprises first electrolyte inlet 4, and second electrolyte inlet 6, first sample inlet 8, and second sample inlet 10, first electrolyte outlet 12, and second electrolyte outlet 14, and first sample outlet 16 and second sample outlet 18. Between first electrolyte inlet 4 and first outlet 12 is first electrolyte chamber 22. Likewise, between second electrolyte inlet 6 and second electrolyte outlet 14 is second electrolyte chamber 24. First sample and second sample inlets and outlets also have connecting chambers. First sample chamber 26 running adjacent to first electrolyte chamber 22 connects first sample inlet 8 to first sample outlet 16. Similarly, second sample chamber 28 running adjacent to second electrolyte chamber 24 connects second sample inlet 10 to second sample outlet 18. Ion-permeable barriers 30 and 32 separate electrolyte chambers 22 and 24 from first sample and second sample chambers 26 and 28, respectively. Between first sample and second sample chambers 26 and 28 is ion-permeable barrier 34. In one embodiment, when in use, first and second electrolyte 36 and 38 occupy first and second electrolyte chambers 22 and 24. It should be understood that during operation, first and second electrolyte 36 and 38, as well as first and second sample 56 and 66 may be stagnant in, or flow through, the respective chambers.

Figure 2:
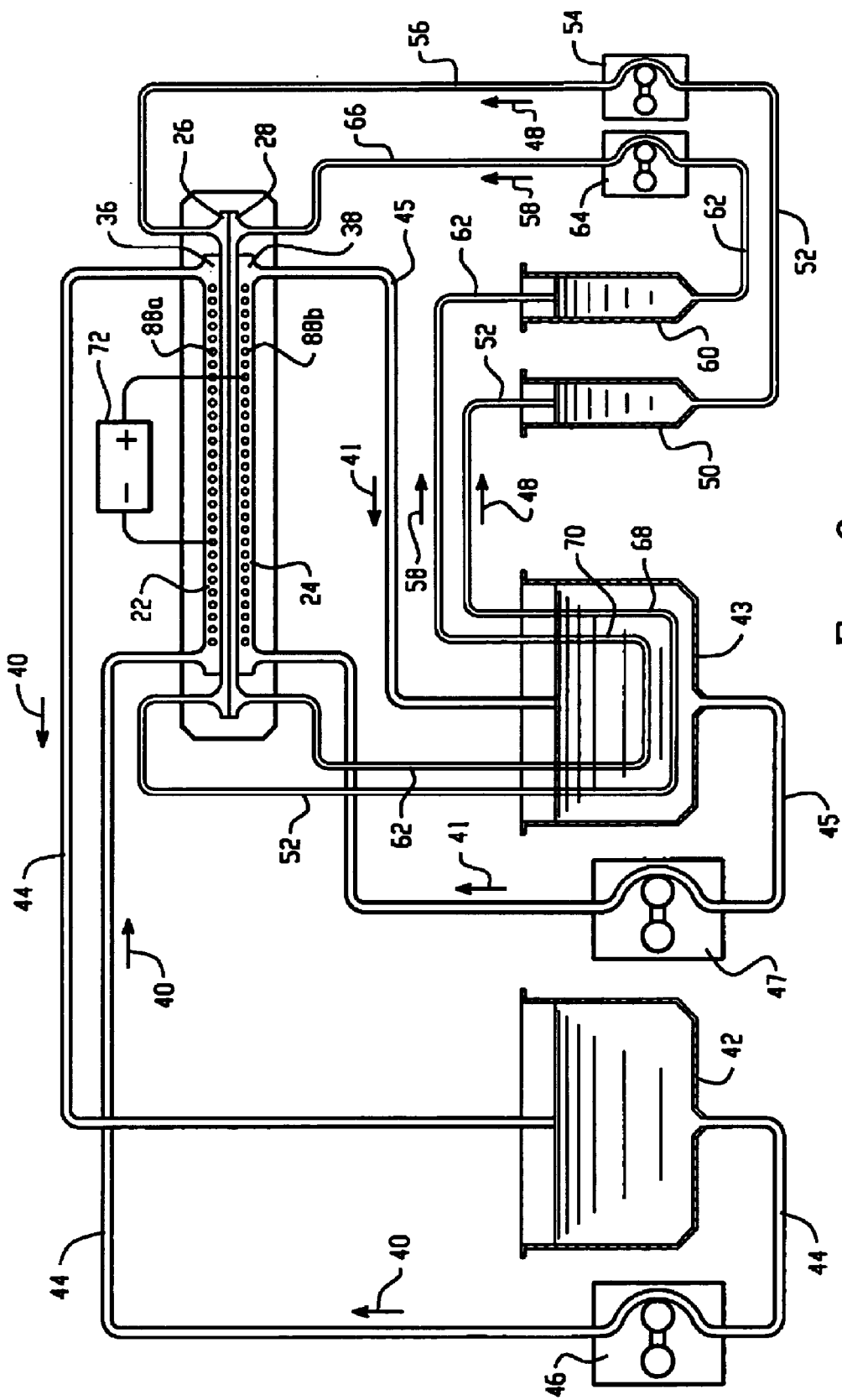
FIG. 2 is a schematic diagram of an apparatus according to the present invention utilizing the separation unit of FIG. 1.

A schematic diagram of an apparatus utilizing separation unit 2 of FIG. 1 is shown in FIG. 2 for the purpose of illustrating the general functionality of an apparatus utilizing the technology of the present invention. In this purely illustrative example, four chambers (first electrolyte chamber 22, second electrolyte chamber 24, first sample chamber 26, and second sample chamber 28) are connected to four flow circuits. First electrolyte flow circuit 40 comprises first electrolyte reservoir 42, electrolyte tubing 44, and electrolyte pump 46. Second electrolyte flow circuit 41 comprises second electrolyte reservoir 43, electrolyte tubing 45, and electrolyte pump 47. In the configuration shown in FIG. 2, electrolyte flow circuits 40 and 41 are running independently from each other so that the composition, temperature, flow rate and volume of first electrolyte 36 and second electrolyte 38 can be suitably adjusted independently of one another.

In the embodiment shown, first electrolyte 36 flows from first electrolyte reservoir 42 through tubing 44 to pump 46 to first electrolyte chamber 22. Second electrolyte 24 flows from second electrolyte reservoir 43 through tubing 45 to pump 47 to second electrolyte chamber 24. First electrolyte 36 flows through inlet 4 and second electrolyte 38 flows through inlet 6. First electrolyte 36 exits separation unit 2 through outlet 12 and second electrolyte 38 exits separation unit 2 through outlet 14. After exiting separation unit 2, electrolytes 36 and 38 flow through tubing 44 and 45 back into respective electrolyte reservoirs 42 and 43. In one embodiment, electrolytes 36 and 38 are held stagnant in electrolyte chambers 22 and 24 during separation. Electrolytes 36 and 38 can also act as a cooling medium and help prevent a build up of gases generated during electrophoresis.

First sample flow circuit 48 contains first sample reservoir 50, tubing 52 and pump 54. First sample 56 flows from first sample reservoir 50 through tubing 52 to pump 54, then through inlet 8 into first sample chamber 26. In one embodiment, the flow directions of first sample 56 and electrolytes 36 and 38 in first sample chamber 26 are opposite. First sample 56 exits separation unit 2 at outlet 16 and flows through tubing 52, then heat exchanger 68 that passes through second electrolyte reservoir 43 before returning to first sample reservoir 50 through tubing 52. In an alternative embodiment, heat exchanger 68 passes through first electrolyte reservoir 42. In another embodiment, the flow directions of first sample 56 and electrolytes 36 and 38 in first sample chamber 26 are the same.

In addition to components of interest, first sample 56 may contain any suitable electrolyte or additive known in the art as demanded by the procedure, application, or separation being performed to substantially prevent or cause migration of selected components through the ion-permeable barriers. In a preferred embodiment, sample from which constituents are to be removed is placed into first sample reservoir 50. However, it is understood that in an alternative embodiment, sample from which constituents are to be removed is placed into second sample reservoir 60.

Similarly, second sample flow circuit 58 contains second sample reservoir 60, tubing 62 and pump 64. Second sample 66 flows from second sample reservoir 60 through tubing 62 to pump 64, then through inlet 10 into second sample chamber 28. In one embodiment, the flow directions of second sample 66 and electrolytes 36 and 38 in second sample chamber 28 are opposite. Second sample 66 exits separation unit 2 at outlet 18 and flows through tubing 62, then heat exchanger 70 that passes through second electrolyte reservoir 43 before returning to second sample reservoir 60 through tubing 62. In an alternative embodiment, heat exchanger 70 passes through first electrolyte reservoir 43.

Second sample 66 may contain any suitable electrolyte or additive known in the art as demanded by the procedure, application, or separation being performed to substantially prevent or cause migration of selected components through the ion-permeable barriers. In a preferred embodiment, sample from which constituents are to be removed is placed into second sample reservoir 60. However, it is understood that in an alternative embodiment, sample from which constituents are to be removed is placed into first sample reservoir 50.

Individually adjustable flow rates of first sample, second sample, first electrolyte and second electrolyte, when employed, can have a significant influence on the separation. Flow rates ranging from zero through several milliliters per minute to several liters per minute are suitable depending on the configuration of the apparatus and the composition, amount and volume of sample processed. In a laboratory scale instrument, individually adjustable flow rates ranging from about 0 mL/minute to about 50,000 mL/minute are used, with the preferred flow rates in the 0 mL/min to about 1,000 mL/minute range. However, higher flow rates are also possible, depending on the pumping means and size of the apparatus. Selection of the individually adjustable flow rates is dependent on the process, the component or components to be transferred, efficiency of transfer, and coupling of the process with other, preceding or following processes.

Preferably, all tubing 44, 52, and 62 is peristaltic tubing that is autoclavable, chemically resistant, and biologically inert. One such tubing is Masterflex® C-FLEX® 50 A tubing. Also, pumps 46, 47, 54 and 64 are preferably peristaltic pumps. In the presently preferred embodiment, heat exchangers 68 and 70 are constructed from stainless steel, although other materials known in the art are suitably used. Preferably, heat exchangers 68 and 70 are autoclavable, chemically resistant, biologically inert and capable of facilitating heat exchange.

Furthermore, it is preferable that first sample flow circuit 48, second sample flow circuit 58, first electrolyte flow circuit 40 and second electrolyte flow circuit 41 are completely enclosed to prevent contamination or cross-contamination. In a preferred embodiment, reservoirs 42, 43, 50, and 60, are completely and individually enclosed from the rest of the apparatus.

The separation unit further comprises electrodes 88a and 88b. Preferably, the respective electrodes are located in the first and second electrolyte chambers and are separated from the first and second sample chambers by ion-permeable barriers.

Electrodes 88a and 88b are suitably standard electrodes or preferably are formed from platinum coated titanium expanded mesh, providing favorable mechanical properties, even distribution of the electric field, long service life and cost efficiency. Electrodes 88a and 88b are preferably located relatively close to ion-permeable barriers 30 and 32 providing better utilization of the applied potential and diminished heat generation. A distance of about 0.1 to 6 mm has been found to be suitable for a laboratory scale apparatus. For scaled-up versions, the distance will depend on the number and type of ion-permeable barriers, and the size and volume of the electrolyte and sample chambers. Preferred distances would be in the order of about 0.1 mm to about 10 mm.

Separation unit 2 also preferably comprises electrode connectors 78 that are used for connecting separation unit 2 to power supply 72. Preferably, power supply 72 is external to separation unit 2, however, separation unit 2 is configurable to accept internal power supply 72. Electrode connectors 78 are preferably autoclavable.

Separation is achieved when an electric potential is applied to separation unit 2. Selection of the electric field strength varies depending on the separation. Typically, the electric field strength varies between 1 V/cm to about 5,000 V/cm, preferably between 10 V/cm to 2,000 V/cm and leads to currents of up to about 1 A. It is preferable to maintain the total power consumption of the unit at the minimum, commensurable with the desired separation and production rate.

In one embodiment, the applied electric potential is periodically stopped and reversed to cause movement of components that have entered the ion-permeable barriers back into at least one of the fluid streams, while substantially not causing re-entry of any components that have entered other fluid streams. In another embodiment, a resting period is utilized. Resting (a period during which fluid flows are maintained but no electric potential is applied) is an optional step that suitably replaces or is included after an optional reversal of the electric potential. Resting is often used for protein-containing samples as an alternative to reversing the potential.

Separation unit 2 is suitably cooled by various methods known in the art such as ice bricks or cooling coils (external apparatus) placed in one or both electrolyte reservoirs 42 and 43, or any other suitable means capable of controlling the temperature of electrolytes 36 and 38. Because both first sample flow circuit 48 and second sample flow circuit 58 pass through either electrolyte reservoir 42 or 43, heat is exchanged between first and second samples and one or both of first and second electrolytes. Heat exchange tends to maintain the temperature in first sample 56 and second sample 66 at the preferred, usually low levels.

In another form, there is provided an electrophoresis unit that comprises four chambers (first electrolyte chamber 22, second electrolyte chamber 24, first sample chamber 26, and second sample chamber 28). Ion-permeable barriers 30 and 32 separate electrolyte chambers 22 and 24 from first sample and second sample chambers 26 and 28, respectively. Between first sample and second sample chambers 26 and 28 is ion-permeable barrier 34. Electrodes are housed in the first and second electrolyte chambers and sample and/or fluid is placed into first sample chamber 26 and second sample chamber 28. In use, an electric potential is applied between the electrodes and one or more components in the first sample chamber 26 or second sample chamber 28 are caused to move to the other sample chamber or to one of the electrolyte chambers.

Figure 3:
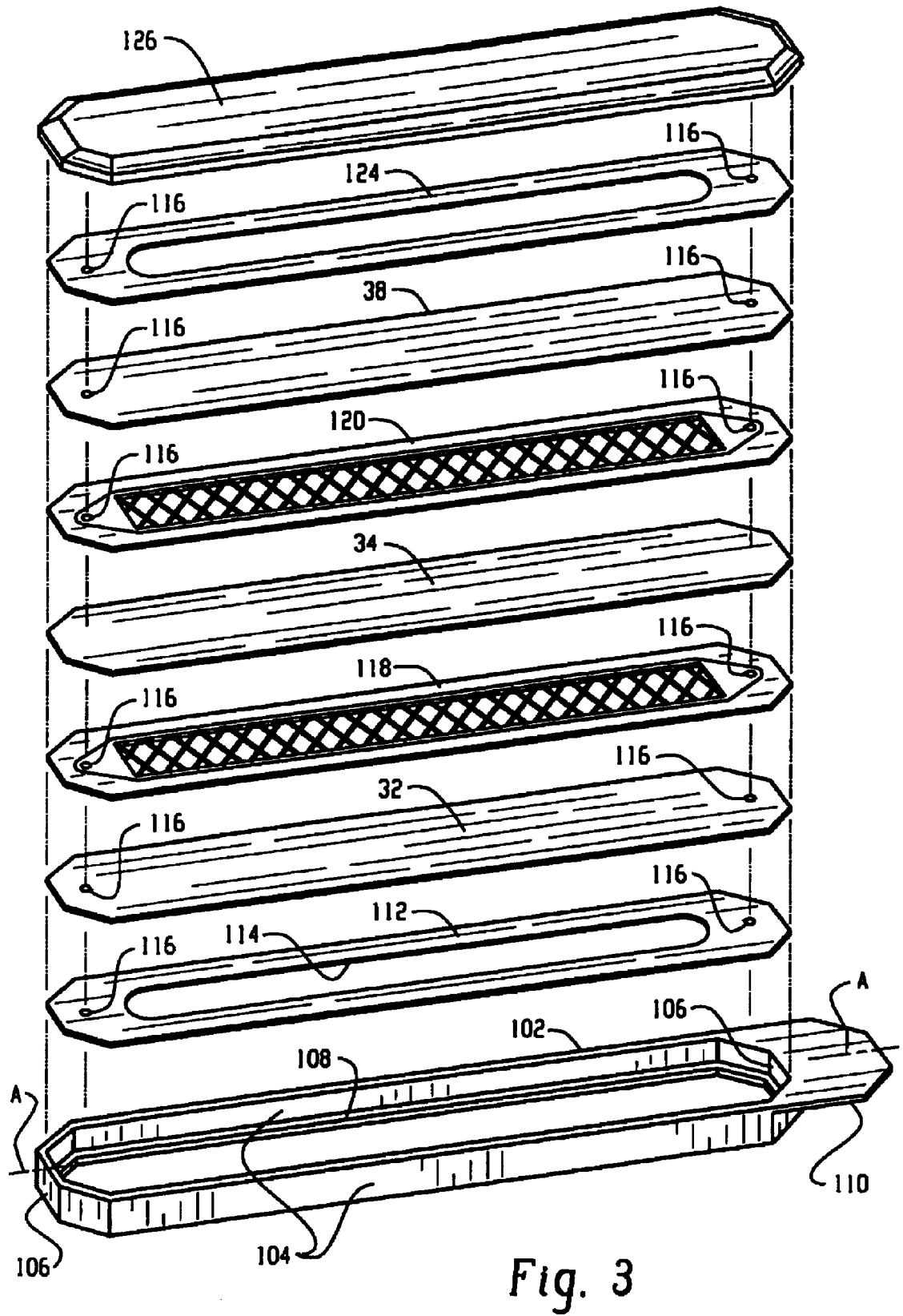
FIG. 3 is an exploded view of a cartridge which may be used with the separation unit of FIG. 1.

FIG. 3 is an exploded view of cartridge 100 which is preferably a modular component of separation unit 2. When configured as a modular unit, cartridge 100 preferably comprises housing 102 for holding in place or encasing the component parts of cartridge 100. In a presently preferred embodiment, cartridge 100 is generally elongated and has side walls 104 which are generally parallel to one another and the longitudinal axis A of cartridge 100. The cartridge is suitably generally octagonal, hexagonal, or ovular. In an octagonal configuration, cartridge 100 has three end walls 106 on each side of side walls 104 forming an octagon. However, two end walls on each side 106 are suitably used to form a hexagon, or one curved end wall 106 on each side is suitably used to form a generally ovular shape. Furthermore, end walls 106 are suitably either straight or generally curved.

Extending around the base of side walls 104 and end walls 106 is a small flange 108 that is generally perpendicular to side walls 104 and end walls 106 and projects inward toward the center of cartridge 100. Along the exterior of either side walls 104 or end walls 106 is preferably a handle 110 to facilitate placement of cartridge 100 into separation unit 2. Flange 108 is preferably configured to interact with lower gasket 112. In a preferred embodiment, lower gasket 112 is generally planar and configured to fit inside walls 104 and 106 of cartridge 100. In a presently preferred embodiment, lower gasket 112 is made from silicon rubber. Lower gasket 112 may be configured so that it has an aperture 114 extending in an elongated manner through the center of lower gasket 112. Also extending through and adjacent each end of lower gasket 112 are alignment holes 116. In a preferred embodiment, alignment holes 116 are circular, forming generally cylindrical channels through lower gasket 112. However, it is also contemplated that alignment holes 116 are suitably triangular, square, rectangular, hexagonal, octagonal, or similarly shaped.

Above lower gasket 112 is a generally planar lower ion-permeable barrier 32. The external shape of ion-permeable barrier 32 is generally the same as that of lower gasket 112 and the interior of cartridge 100 so that ion-permeable barrier 32 is configured to fit inside cartridge 100. Like lower gasket 112, ion-permeable barrier 32 preferably has two alignment holes of the same location and configuration as alignment holes 116 in lower gasket 112. Ion-permeable barrier 32 substantially prevents convective mixing of the contents of first electrolyte chamber 22 and first sample chamber 26, while permits selective trans-barrier transport of selected constituents upon application of the electric potential.

In one embodiment, ion-permeable barrier 32 is formed from a membrane with a characteristic average pore size and pore-size distribution. The average pore size and pore size distribution of the membrane is selected to facilitate trans-membrane transport of certain constituents, while substantially preventing trans-membrane transport of other constituents.

In another embodiment, ion-permeable barrier 32 is an isoelectric ion-permeable barrier, such as an isoelectric membrane that substantially prevents convective mixing of the contents of first electrolyte chamber 22 and first sample chamber 26, while permits selective trans-barrier transport of selected constituents upon application of the electric potential. Suitable isoelectric membranes can be produced by copolymerizing acrylamide, N,N'-methylene bisacrylamide and appropriate acrylamido derivatives of weak electrolytes yielding isoelectric membranes with pI values in the 2 to 12 range, and average pore sizes that either facilitate or substantially prevent trans-membrane transport of components of selected sizes.

Above lower ion-permeable barrier 32 is lower grid element 118 that is generally planar and also shaped like lower gasket 112 and the interior of cartridge 100 so that lower grid element 118 is configured to fit inside cartridge 100. One of the functions of lower grid element 118 is to separate lower ion-permeable barrier 32 from ion-permeable barrier 34. Another function of lower grid element 118 is to provide a flow path for first sample 56. Like lower ion-permeable barrier 32 and lower gasket 112, lower grid element 118 suitably also has alignment holes 116.

Above lower grid element 118 is generally planar ion-permeable barrier 34. The external shape of ion-permeable barrier 34 is generally the same as that of lower gasket 112 and the interior of cartridge 100 so that ion-permeable barrier 34 is configured to fit inside cartridge 100. Ion-permeable barrier 34 substantially prevents convective mixing of the contents of first sample chamber 26 and second sample chamber 28, while permits selective trans-barrier transport of selected constituents upon application of the electric potential.

In one embodiment, ion-permeable barrier 34 is formed from a membrane with a characteristic average pore size and pore-size distribution. The average pore size and pore size distribution of the membrane is selected to facilitate trans-membrane transport of certain constituents, while substantially preventing trans-membrane transport of other constituents.

In another embodiment, ion-permeable barrier 34 is an isoelectric ion-permeable barrier, such as an isoelectric membrane that substantially prevents convective mixing of the contents of first sample chamber 26 and second sample chamber 28, while permits selective trans-barrier transport of selected constituents upon application of the electric potential. Suitable isoelectric membranes can be produced by copolymerizing acrylamide, N,N'-methylene bisacrylamide and appropriate acrylamido derivatives of weak electrolytes yielding isoelectric membranes with pI values in the 2 to 12 range, and average pore sizes that either facilitate or substantially prevent trans-membrane transport of components of selected sizes.

Above ion-permeable barrier 34 are three upper components: upper grid element 120, upper ion-permeable barrier 38, and upper gasket 124. These three components are placed so that upper grid element 120 is immediately above ion-permeable barrier 34, ion-permeable barrier 38 is immediately above upper grid element 120, and upper gasket 124 is immediately above ion-permeable barrier 38. The configuration of the three upper components suitably mirrors that of the lower three components.

Components below ion-permeable barrier 34 having alignment holes 116 may be connected together with a fastener, which is any type of connector configured to interact with alignment holes 116 and facilitate through flow of first sample 56. Similarly, components above ion-permeable barrier 34 having alignment holes 116 may be connected together with a fastener, which is any type of connector configured to interact with alignment holes 116 and facilitate through flow of second sample 66.

Components of cartridge 100 are suitably held in cartridge 100 by clip 126. Clip 126 is suitably snap fitted or glued around the top of walls 104 and 106 of cartridge 100.

Ion-permeable barrier 38 substantially prevents convective mixing of the contents of second electrolyte chamber 24 and second sample chamber 28, while permits selective trans-barrier transport of selected constituents upon application of the electric potential.

In one embodiment, ion-permeable barrier 38 is formed from a membrane with a characteristic average pore size and pore-size distribution. The average pore size and pore size distribution of the membrane is selected to facilitate trans-membrane transport of certain constituents, while substantially preventing trans-membrane transport of other constituents.

In another embodiment, ion-permeable barrier 38 is an isoelectric ion-permeable barrier, such as an isoelectric membrane that substantially prevents convective mixing of the contents of second electrolyte chamber 24 and second sample chamber 28, while permits selective trans-barrier transport of selected constituents upon application of the electric potential. Suitable isoelectric membranes can be produced by copolymerizing acrylamide, N,N'-methylene bisacrylamide and appropriate acrylamido derivatives of weak electrolytes yielding isoelectric membranes with pI values in the 2 to 12 range, and average pore sizes that facilitate or substantially prevent trans-membrane transport of components of selected sizes.

Preferred grid elements 118 and 120 are shown in more detail in FIGS. 4 to 7. FIG. 4A shows a plan view of a preferred grid element which is incorporated as a component of cartridge 100 for separation unit 2. An elongate rectangular cut-out portion 128 which incorporates lattice 131 is defined in the center of the grid element. At each end of the grid element, an alignment hole 116 is suitably provided for alignment with the other components of cartridge 100. Preferably, a triangular channel area 130 having sides and a base, extends and diverges from each alignment hole 116 to cut-out portion 128. Upstanding ribs 132, 134, and 136 (best shown in FIGS. 6 and 7) are defined in channel area 130. Liquid flowing through hole 116 thus passes along triangular channel area 130 between ribs 132, 134, and 136 and into lattice 131. Ribs 132, 134, and 136 direct the flow of liquid from hole 116 so that they help ensure that liquid is evenly distributed along the cross-section of lattice 131. Ribs 132, 134, and 136 also provide support to ion-permeable barrier 34 disposed above or below the grid element.

Lattice 131 comprises a first array of spaced parallel members 138 extending at an angle to the longitudinal axis of the grid disposed above and integrally formed with a second lower set of spaced parallel members 140 extending at approximately twice the angle of the first array of parallel members 138 to the longitudinal axis of the grid. In the presently preferred embodiment, the first array of parallel members 138 extend at approximately a 45 degree angle from the longitudinal axis and the second array of parallel members 140 extend at approximately 90 degrees to the first array of parallel members 138, however, other angles are also suitably used.

Figure 4A:
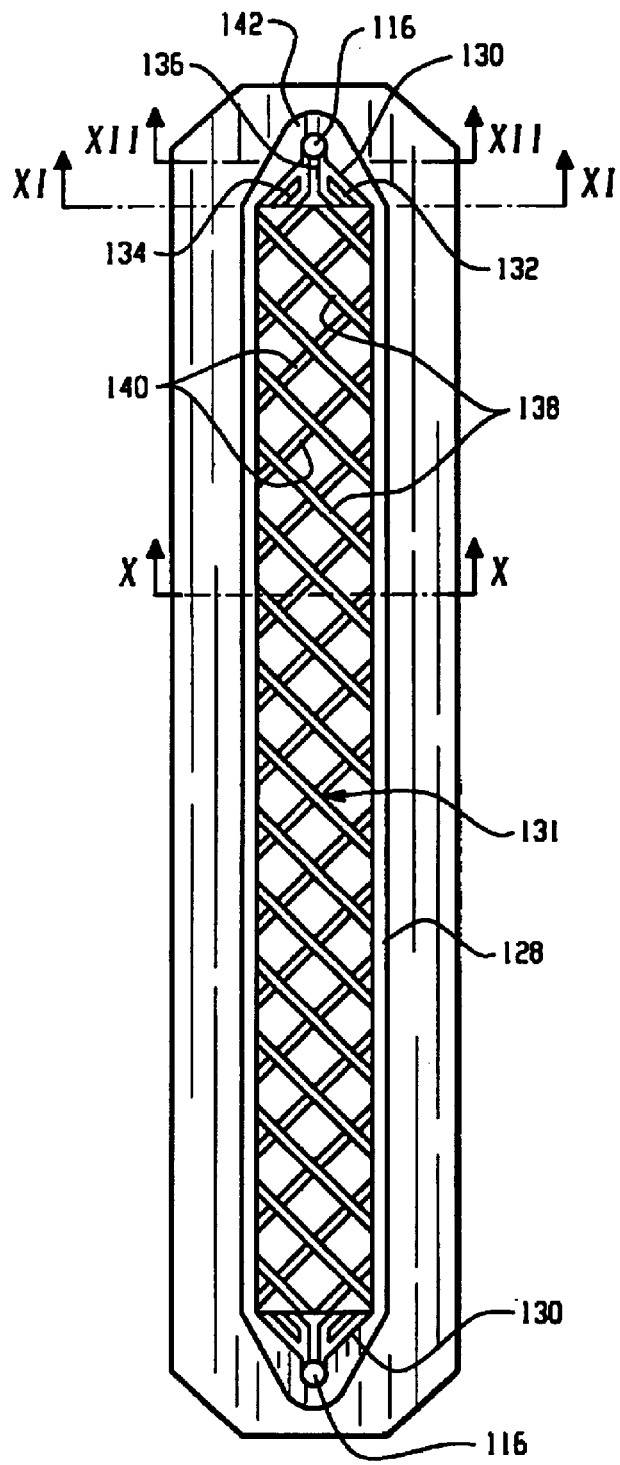
FIG. 4A is a plan view of a grid element which may be incorporated as a component of a cartridge of a separation unit.
Figure 4B:
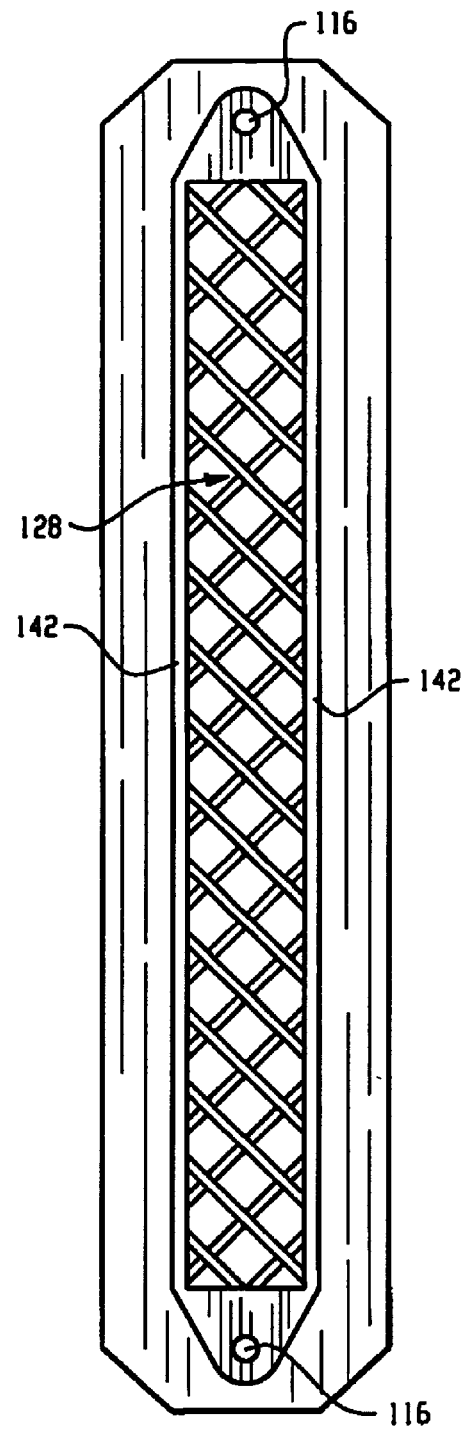
FIG. 4B is a reverse plan view of the grid element of FIG. 4A.

Referring to FIG. 4B, the reverse side of the grid element is illustrated. The reverse side is suitably relatively smooth and flat aside from cut-out area 128 and alignment holes 116. The smooth, flat surface tends to ensure sealing between ion-permeable barriers 32 and grid element 118, and ion-permeable barrier 38 and grid element 120, respectively.

Referring to FIG. 5, the upper and lower surfaces of first and second parallel members 138 and 140 are preferably rounded. When parallel members 138 and 140 are rounded, the absence of any sharp edges help prevent damage to ion-permeable barrier 34 and provide extra support. Lattice 131 evenly distributes the flow of liquid over the surface of ion-permeable barrier 34. The use of a first set of members 138 disposed above a second set of members 140 tends to ensure that the liquid in a stream is forced to move up and down, changing direction frequently, which helps to encourage mixing of the liquid and tends to inhibit static flow zones.

The thickness of the grid element is preferably relatively small. In one presently preferred embodiment, exterior areas 144 of the element are 0.8 mm thick. Sealing ridge 142 (also shown in FIGS. 4A and 4B) extends around the periphery of lattice 131 to improve sealing. Ridge 142 is preferably approximately 1.2 mm thick measured from one side of the grid element to the other. The distance between the opposite peaks of lattice elements 138 and 140 measured from one side of the grid to the other is preferably approximately 1 mm. The relatively small thickness of the grid provides several advantages. First, it results in a more even distribution of liquid over ion-permeable barrier 34 and assists in inhibiting its fouling by macromolecules.

Also, the volume of liquid required is decreased by the use of a relatively thin grid which enables relatively small sample volumes to be used for laboratory-scale separations, a significant advantage over prior art separation devices.

Finally, if the electric field strength is maintained constant, the use of a relatively thinner grid element enables less electrical power to be deposited into the liquid. If less heat is transferred into the liquid, the temperature of the liquid remains lower. This is advantageous, since high temperatures may destroy both the sample and the desired product.

Figure 8:
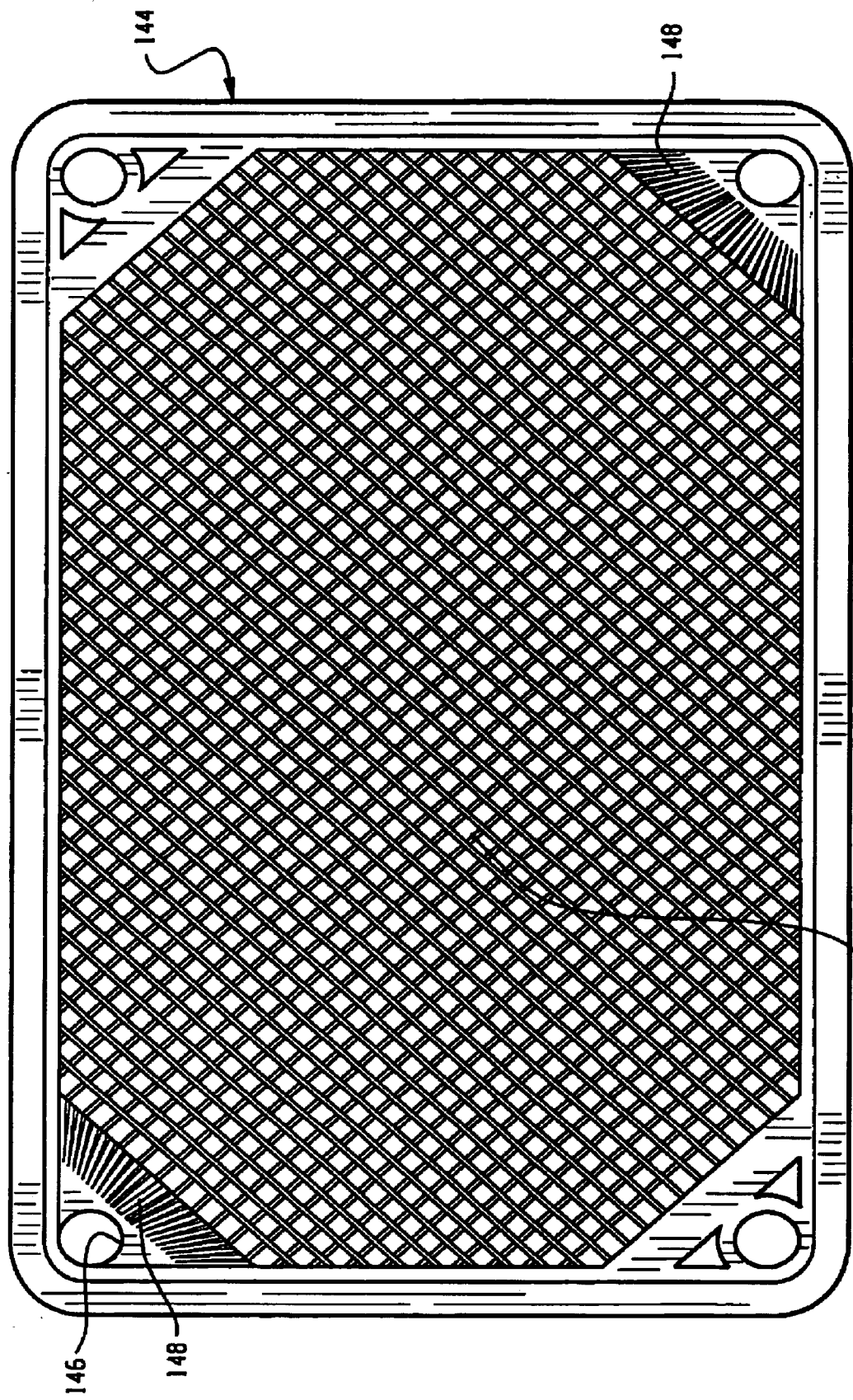
FIG. 8 is a plan view of an alternative embodiment of a grid element which may be incorporated as a component of a cartridge of a separation unit.

FIG. 8 illustrates grid element 144 for an alternative embodiment of the present invention. Grid element 144 utilizes an ion-permeable barrier having a much larger surface area than that of grid elements 118 and 120. The principal operation of grid element 144 is suitably generally the same as that of the smaller grid elements although holes 146 through which first sample 56 or second sample 66 are fed are located in two opposite corners of grid 144 and there are many more channels 148 feeding streams from holes 146 to central portion 150 of grid 144. The cartridge, cartridge casing, and other components are increased in size and shape so as to match that of grid 144.

Figure 9:
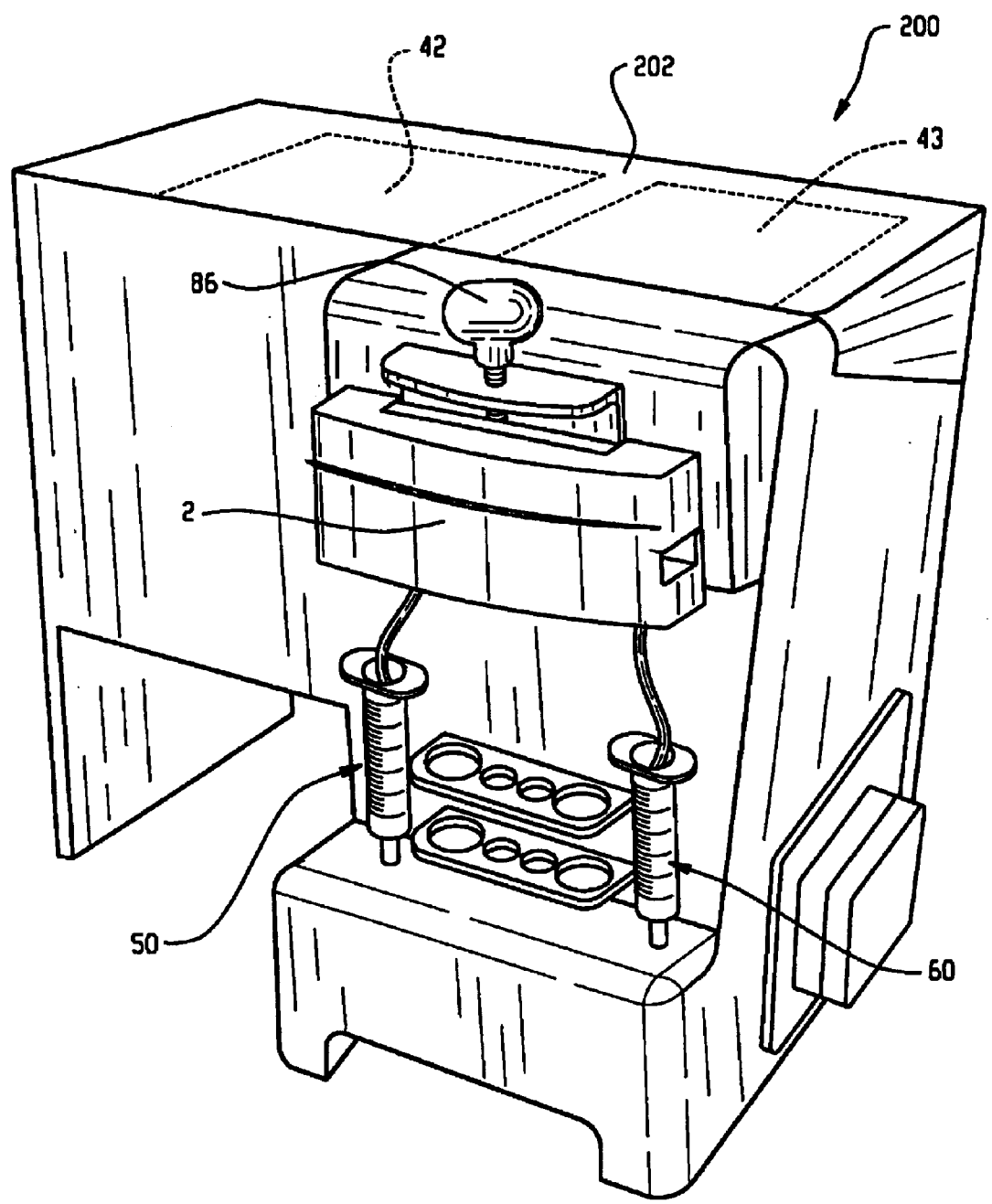
FIG. 9 shows an apparatus utilizing the separation unit of FIG. 1.

FIG. 9 is a diagram of a presently preferred embodiment of a separation apparatus 200 for use in accordance with the present invention. The separation apparatus comprises separation unit 2 configured to accept cartridge 100 and clamp 86. Clamp 86 is used to fix separation unit 2 in place once a component cartridge is placed into separation unit 2. In the presently preferred embodiment, clamp 86 is constructed from aluminum and is preferably anodized. Clamp 86 is preferably a simple screw clamp unit so that a screw-operated knob may be used to open and close clamp 86. The separation apparatus shows first sample reservoir 50, second sample reservoir 60, and first and second electrolyte reservoirs 42 and 43 in electrolyte compartment 202.

In order that the present invention may be more clearly understood, examples of separation methodology are described with reference to the preferred forms of the separation technology as described.

EXAMPLE 1

An apparatus according to the present invention, shown in FIG. 9, was used to separate the proteins present in chicken egg-white into two fractions. An electrophoresis separation cartridge, shown in FIGS. 3 to 7, was adapted to be used in the apparatus. The first ion-permeable barrier placed between the first electrolyte chamber and the first sample chamber was a pI=4.0 isoelectric membrane prepared from Immobiline chemicals (Pharmacia, Sweden), acrylamide and N-N'-methylene bis-acrylamide. The second ion-permeable barrier placed between the first sample chamber and the second sample chamber was a pI=5.0 isoelectric membrane prepared from Immobiline chemicals (Pharmacia, Sweden), acrylamide and N-N'-methylene bis-acrylamide. The third ion-permeable barrier placed between the second sample chamber and the second electrolyte chamber was a pI=7.0 isoelectric membrane prepared from Immobiline chemicals (Pharmacia, Sweden), acrylamide and N-N'-methylene bis-acrylamide.

The first electrolyte reservoir was filled with 60 mL of an 80 mM acetic acid solution, pH 2.9. The second electrolyte reservoir was filled with 60 mL of an 8 mM triethanol amine solution, pH 9.9. The first and second sample reservoirs were filled with 30 mL each of a filtered chicken egg-white solution, diluted with deionized water at a rate of 1 to 25. The anode was placed into the first electrolyte chamber, the cathode into the second electrolyte chamber. The applied potential was 250 V, the separation time was 15 minutes. Aliquots were taken for analysis from the sample reservoirs before separation and at the end of the separation.

Full-column-imaging capillary isoelectric focusing on an iCE280 instrument (Convergent Bioscience, Toronto, Canada) was used to analyze the egg-white samples. The fused silica separation capillary was 5 cm long, its internal diameter was 100 micrometer. The focusing medium contained 8% carrier ampholytes to cover the pH 3–10 range, in an aqueous, 0.1% methylcellulose solution. Seventy-five microliter of the sample to be analyzed was mixed with 150 microliter of the focusing medium, filled into the capillary and focused for 5 minutes at 3,000 V. Dansyl phenylalanine (pI=3.52) and terbutaline (pI=9.61) were used as pI markers.

Figure 10:
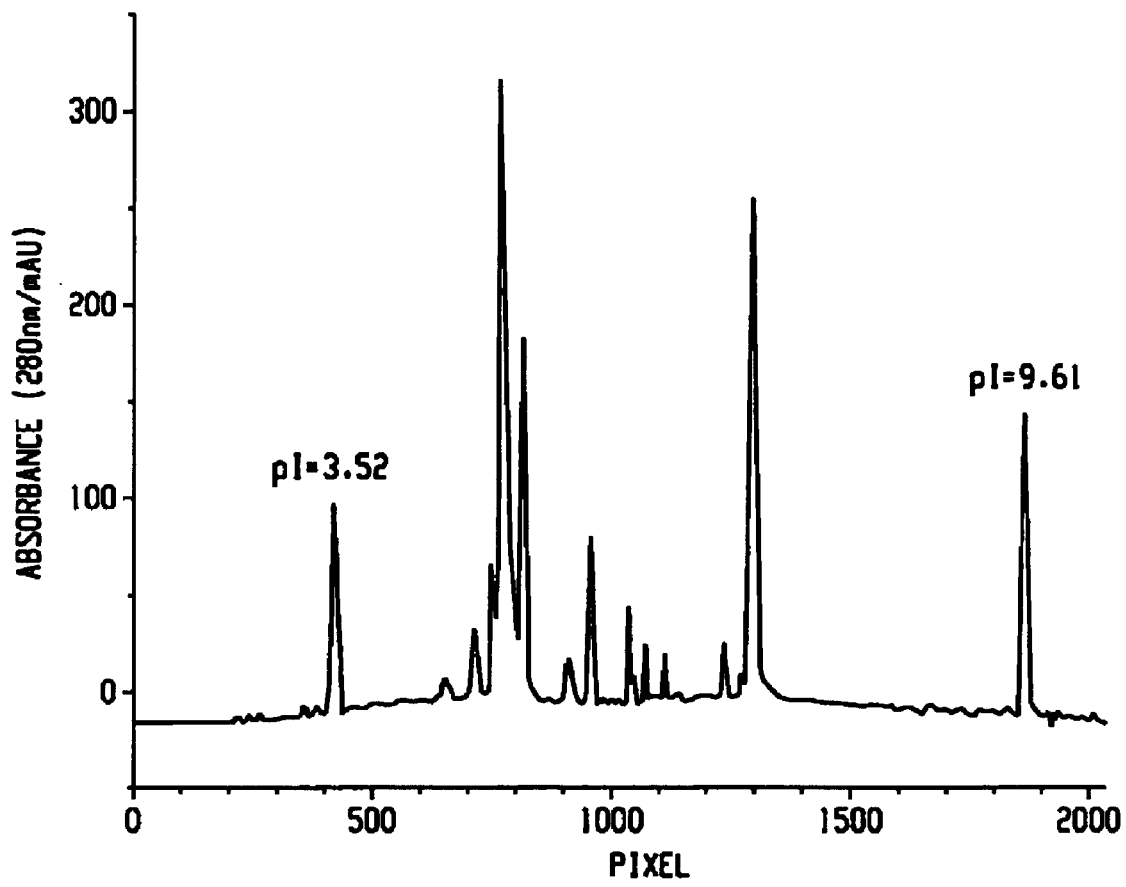
FIG. 10 shows the image, at 280 nm, of the protein bands separated by the iCE280 full-column-imaging capillary isoelectric focusing instrument, from a chicken egg-white sample, used as the starting material for the electrophoretic separation experiments described in Examples 1 to 3. The peaks labeled pI 3.52 and pI 9.61 correspond to dansyl phenylalanine and terbutaline, respectively, used as isoelectric point markers. The egg-white sample was diluted 1:25 with deionized water and filtered prior to analysis. Analysis conditions: instrument: iCE280 full-column imaging capillary IEF system, separation capillary: 5 cm long, 100 micrometer I.D. fused silica, focusing medium: 8% carrier ampholytes for pH 3–10 in aqueous 0.1% methylcellulose solution, focusing time: 5 minutes, applied potential: 3,000 V.

FIG. 10 shows the results for the egg-white feed sample. The peaks between pixels 650 and 850 correspond to ovalbumin isoforms, those between pixels 1250 and 1350 correspond to ovotransferrin isoforms.

Figure 11:
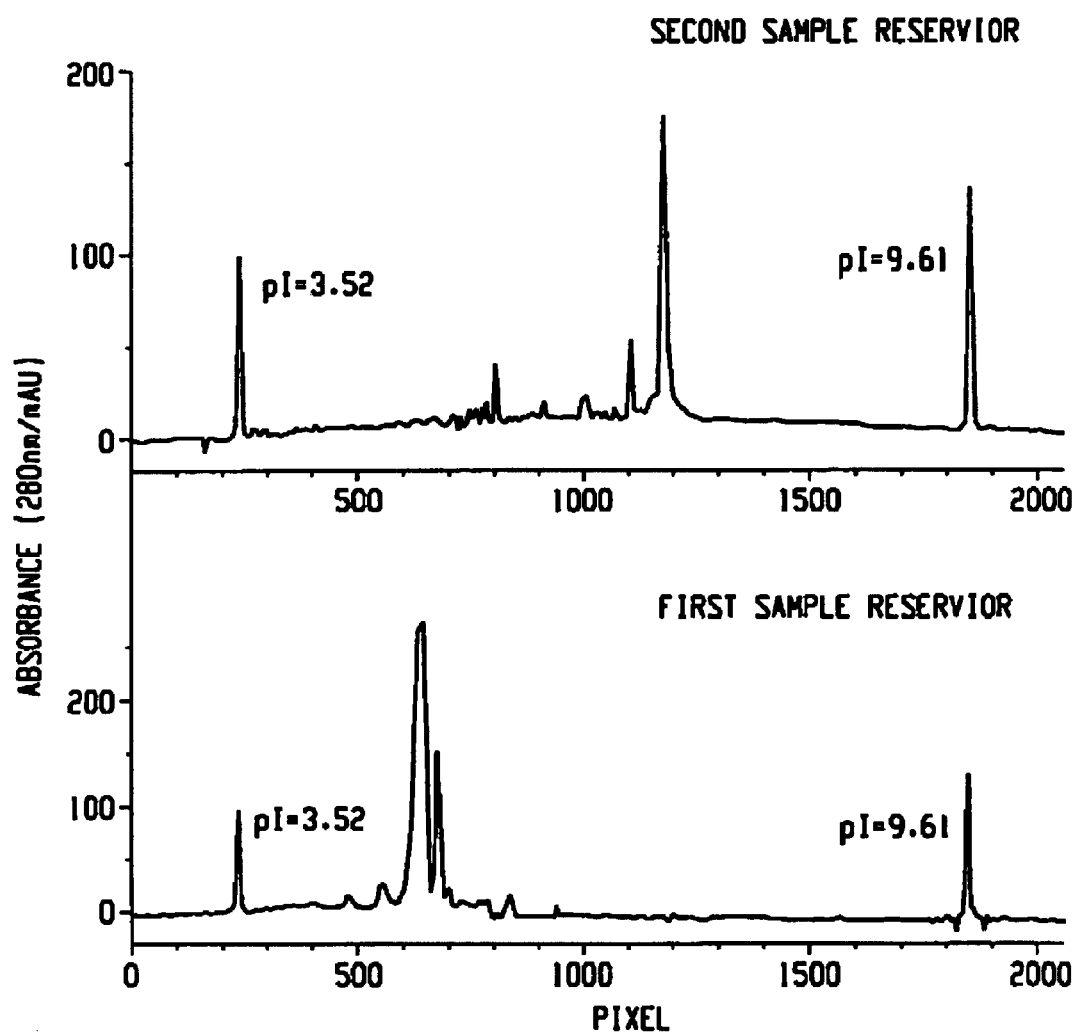
FIG. 11 shows the image, at 280 nm, of the protein bands separated by the iCE280 full-column-imaging capillary isoelectric focusing instrument, from aliquots collected at the end of the experiment from the first sample reservoir (bottom panel) and second sample reservoir (top panel) of the electrophoretic apparatus disclosed here and described in Example 1. Separation conditions: anolyte: 60 mL of 80 mM acetic acid, pH=2.9, catholyte: 60 mL 8 mM triethanol amine, pH=9.9, sample: 60 mL aqueous egg-white sample diluted 1:25 in deionized water, separation time: 15 minutes, applied potential: 250 V, first ion-permeable barrier between the first electrolyte chamber and the first sample chamber: pI=4.0 isoelectric membrane, second ion-permeable barrier between the first sample chamber and the second sample chamber: pI=5.0 isoelectric membrane, third ion-permeable barrier between the second sample chamber and the second electrolyte chamber: pI=7.0 isoelectric membrane. The peaks labeled pI 3.52 and pI 9.61 correspond to dansyl phenylalanine and terbutaline, respectively, used as isoelectric point markers. Analysis conditions: instrument: iCE280 full-column imaging IEF system, capillary: 5 cm long, 100 micrometer I.D. fused silica, focusing medium: 8% carrier ampholytes for pH 3–10 in aqueous 0.1% methylcellulose solution, focusing time: 5 minutes, applied potential: 3,000 V.

As a result of the electrophoretic separation, proteins with pI values lower than 5.0, such as ovalbumin (pI=4.7), accumulated in the first sample reservoir, on the anodic side of the pI=5.0 isoelectric membrane (bottom panel in FIG. 11). Proteins with pI values greater than 5.0, such as ovotransferrin (pI=6.1) accumulated in the second sample reservoir, on the cathodic side of the isoelectric membrane (top panel in FIG. 11).

EXAMPLE 2

The same apparatus as in Example 1 was used to separate the proteins present in chicken egg-white into two fractions. An electrophoresis separation cartridge, shown in FIGS. 3 to 7, was adapted to be used in the apparatus. The first ion-permeable barrier placed between the first electrolyte chamber and the first sample chamber was a polyacrylamide membrane with a nominal molecular mass cut-off of 5,000 dalton. The ion-permeable barrier between the first sample chamber and the second sample chamber was a pI 5.0 isoelectric membrane prepared from Immobiline chemicals (Pharmacia, Sweden), acrylamide and N-N'-methylene bis-acrylamide as in Example 1. The third ion-permeable barrier placed between the second sample chamber and the second electrolyte chamber was a polyacrylamide membrane with a nominal molecular mass cut-off of 5,000 dalton.

The first electrolyte reservoir was filled with 60 mL of a 2 mM acetic acid solution, pH 3.8. The second electrolyte reservoir was filled with 60 mL of an 8 mM triethanol amine solution, pH 9.9. The first and second sample reservoirs were filled with 30 mL each of a filtered chicken egg-white solution, diluted with deionized water at a rate of 1 to 25. The anode was placed into the first electrolyte chamber, the cathode into the second electrolyte chamber. The applied potential was 250 V, the separation time was 15 minutes. Aliquots were taken for analysis from the sample reservoirs at the end of the separation.

Full-column-imaging capillary isoelectric focusing on an iCE280 instrument (Convergent Bioscience, Toronto, Canada) was used to analyze the egg-white samples. The fused silica separation capillary was 5 cm long, its internal diameter was 100 micrometer. The focusing medium contained 8% carrier ampholytes to cover the pH 3–10 range, in an aqueous, 0.1% methylcellulose solution. Seventy-five microliter of the sample to be analyzed was mixed with 150 microliter of the focusing medium, filled into the capillary and focused for 5 minutes at 3,000 V. Dansyl phenylalanine (pI=3.52) and terbutaline (pI=9.61) were used as pI markers.

Figure 12:
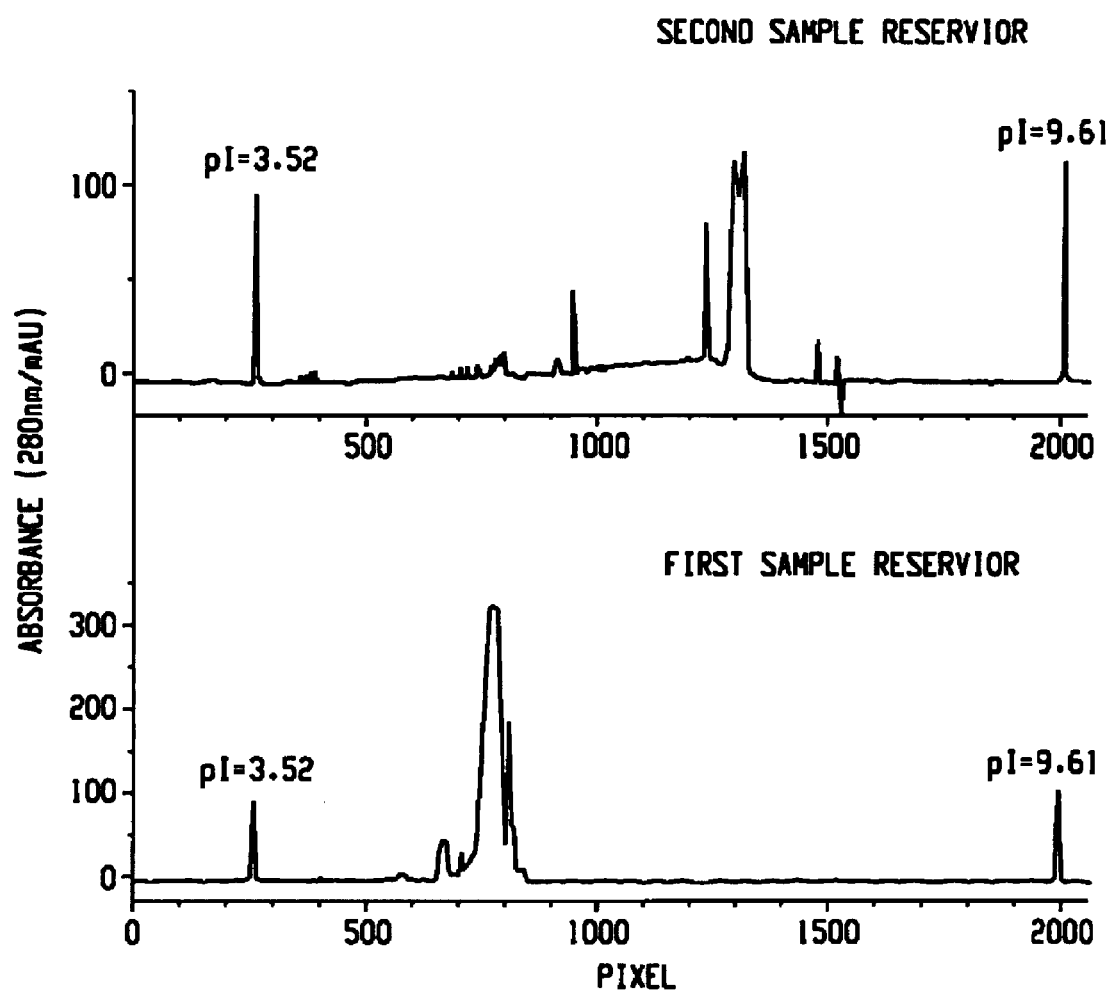
FIG. 12 shows the image, at 280 nm, of the protein bands separated by the iCE280 full-column-imaging capillary isoelectric focusing instrument, from aliquots collected at the end of the experiment described in Example 2 from the first sample reservoir (bottom panel) and the second sample reservoir (top panel) of the electrophoretic apparatus disclosed here. Separation conditions: anolyte: 60 mL 2 mM acetic acid, catholyte: 60 mL 8 mM triethanol amine, sample: 60 mL aqueous egg-white sample diluted 1:25 in distilled water, separation time: 15 minutes, applied potential: 250 V, first ion-permeable barrier between the first electrolyte chamber and the first sample chamber: polyacrylamide membrane with a nominal molecular mass cut-off of 5,000 dalton, second ion-permeable barrier between the first sample chamber and the second sample chamber: pI=5.0 isoelectric membrane, third ion-permeable barrier between the second sample chamber and the second electrolyte chamber: polyacrylamide membrane with a nominal molecular mass cut-off of 5,000 dalton. The peaks labeled pI 3.52 and pI 9.61 correspond to dansyl phenylalanine and terbutaline, respectively, used as isoelectric point markers. Analysis conditions: instrument: iCE280 full-column imaging IEF system, capillary: 5 cm long, 100 micrometer I.D. fused silica, focusing medium: 8% carrier ampholytes for pH 3–10 in aqueous 0.1% methylcellulose solution, focusing time: 5 minutes, applied potential: 3,000 V.

As a result of the electrophoretic separation, proteins with pI values lower than 5.0, such as ovalbumin (pI=4.7), accumulated in the first sample reservoir, on the anodic side of the pI=5.0 isoelectric membrane (bottom panel in FIG. 12). Proteins with pI values greater than 5.0, such as ovotransferrin (pI=6.1) accumulated in the second sample reservoir, on the cathodic side of the pI=5.0 isoelectric membrane (top panel in FIG. 12). Neither ovalbumin nor ovotransferrin were lost into the first or second electrolyte chambers despite the fact that the first and third ion-permeable barriers were not isoelectric membranes as in Example 1. At the end of the separation, the solution pH in the first and second sample reservoirs was 4.7 and 6.7, respectively.

EXAMPLE 3

The same apparatus as in Example 1 was used to separate the proteins present in chicken egg-white into two fractions. The first ion-permeable barrier placed between the first electrolyte chamber and the first sample chamber was a polyacrylamide membrane with a nominal molecular mass cut-off of 1,000,000 dalton. The ion-permeable barrier between the first sample chamber and the second sample chamber was a pI 5.0 isoelectric membrane prepared from Immobiline chemicals (Pharmacia, Sweden), acrylamide and N-N'-methylene bis-acrylamide as in Example 1. The third ion-permeable barrier placed between the second sample chamber and the second electrolyte chamber was a polyacrylamide membrane with a nominal molecular mass cut-off of 1,000,000 dalton.

The first electrolyte reservoir was filled with 60 mL of a 2 mM acetic acid solution, pH 3.8. The second electrolyte reservoir was filled with 60 mL of an 8 mM triethanol amine solution, pH 9.9. The first and second sample reservoirs were filled with 30 mL each of a filtered chicken egg-white solution, diluted with deionized water at a rate of 1 to 25. The anode was placed into the first electrolyte chamber, the cathode into the second electrolyte chamber. The applied potential was 250 V, the separation time was 15 minutes. Aliquots were taken for analysis from the sample reservoirs at the end of the separation, and analyzed by full-column-imaging capillary isoelectric focusing on an iCE280 instrument.

Figure 13:
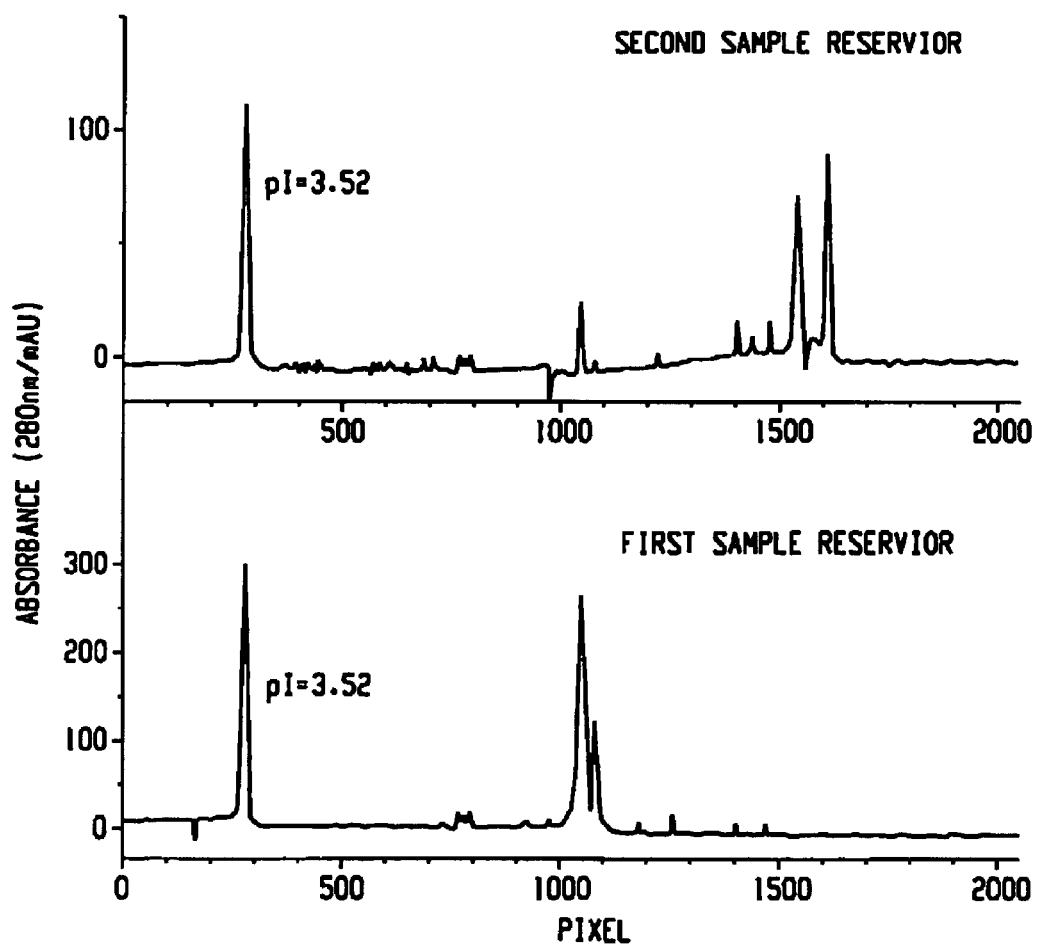
FIG. 13 shows the image, at 280 nm, of the protein bands separated by the iCE280 full-column-imaging capillary isoelectric focusing instrument, from aliquots collected at the end of the experiment described in Example 3 from the first sample reservoir (bottom panel) and the second sample reservoir (top panel) of the electrophoretic apparatus disclosed here. Separation conditions: anolyte: 60 mL 2 mM acetic acid, catholyte: 60 mL 8 mM triethanol amine, sample: 60 mL aqueous egg-white sample diluted 1:25 in deionized water, separation time: 15 minutes, applied potential: 250 V, first ion-permeable barrier between the first electrolyte chamber and the first sample chamber: polyacrylamide membrane with a nominal molecular mass cut-off of 1,000,000 dalton, second ion-permeable barrier between the first sample chamber and the second sample chamber: pI=5.0 isoelectric membrane, third ion-permeable barrier between the second sample chamber and the second electrolyte chamber: polyacrylamide membrane with a nominal molecular mass cut-off of 1,000,000 dalton. The peak labeled pI 3.52 corresponds to dansyl phenylalanine, used as isoelectric point marker. Analysis conditions: instrument: iCE280 full-column imaging IEF system, capillary: 5 cm long, 100 micrometer I.D. fused silica, focusing medium: 8% carrier ampholytes for pH 3–10 in aqueous 0.1% methylcellulose solution, focusing time: 5 minutes, applied potential: 3,000 V.

As a result of the electrophoretic separation, proteins with pI values lower than 5.0, such as ovalbumin (pI=4.7), accumulated in the first sample reservoir, on the anodic side of the pI=5.0 isoelectric membrane (bottom panel in FIG. 13). Proteins with pI values greater than 5.0, such as ovotransferrin (pI=6.1) accumulated in the second sample reservoir, on the cathodic side of the pI=5.0 isoelectric membrane (top panel of FIG. 13). Neither ovalbumin nor ovotransferrin were lost into the first or second electrolyte chambers despite the fact that the average pore size of the first and third ion-permeable barriers was large enough to permit their passage through these barriers. At the end of the separation, the solution pH in the first and second sample reservoirs was 4.7 and 6.2, respectively.

EXAMPLE 4

The same apparatus as in Example 1 was used to purify immunoglobulin G (IgG) from human plasma. The first ion-permeable barrier placed between the first electrolyte chamber and the first sample chamber was a polyacrylamide membrane with a nominal molecular mass cut-off of 150,000 dalton. The ion-permeable barrier between the first sample chamber and the second sample chamber was a pI 5.8 isoelectric membrane prepared from Immobiline chemicals (Pharmacia, Sweden), acrylamide and N-N'-methylene bis-acrylamide. The third ion-permeable barrier placed between the second sample chamber and the second electrolyte chamber was a polyacrylamide membrane with a nominal molecular mass cut-off of 150,000 dalton.

The first electrolyte reservoir was filled with 2 L of a 2 mM 5-amino caproic acid solution that also contained 5 mM NaCl, its pH was adjusted to 4.8 with HCl. The second electrolyte reservoir was filled with 2 L of a 2 mM MOPSO solution that also contained 5 mM NaCl, its pH was adjusted to 6.8 with NaOH. The anode was placed into the first electrolyte chamber, the cathode into the second electrolyte chamber. The applied potential was 250 V. Initially, both sample reservoirs were filled with deionized water. Potential was applied for 2 minutes to remove any unpolymerized material from the membranes. After 2 minutes, all reservoirs were emptied, the electrolyte reservoirs were refilled with fresh electrolytes, the sample reservoirs were filled with 15 mL each of human plasma diluted 1 to 3 with deionized water. Potential was applied for 40 minutes. Aliquots were taken for analysis from the sample reservoir chambers at 0, 10, 20, and 40 minutes, respectively.

Figure 14:
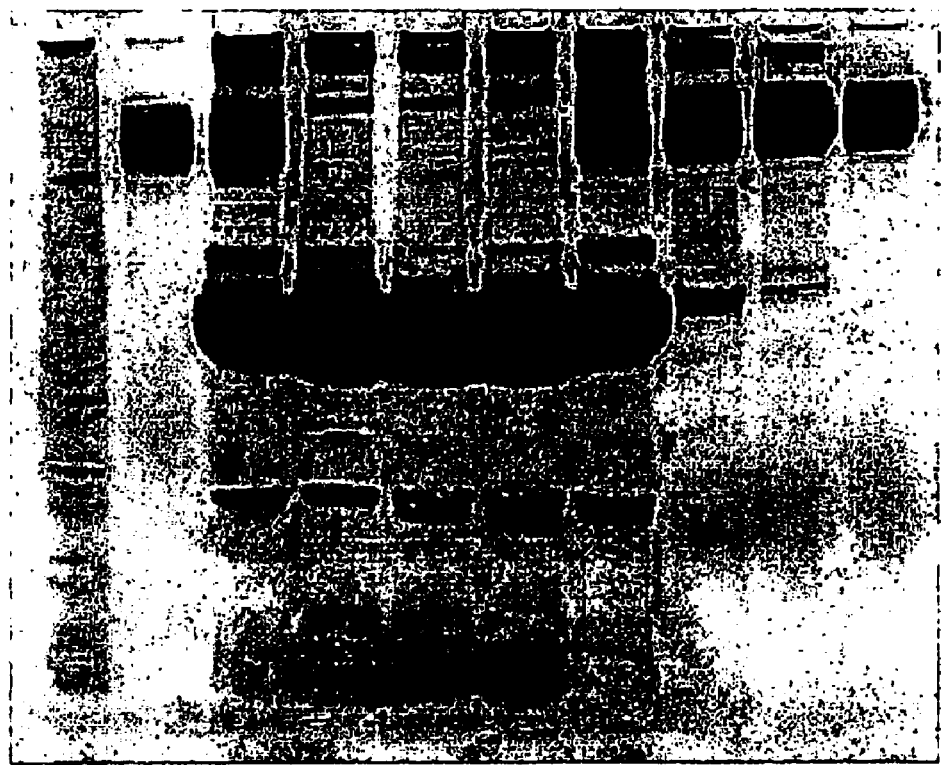
FIG. 14 shows the image of an SDS-PAGE gel used to analyze the protein bands present in the aliquots collected from the first and second sample reservoirs of the electrophoretic apparatus disclosed here and described in Example 4 during the isolation of IgG from human plasma. Molecular weight markers (Sigma, St. Louis, Mo., USA) were applied onto Lane 1, a pharmaceutical-grade IgG preparation used as reference material onto Lane 2. Samples taken at 0, 10, 20, and 40 minutes respectively from the first sample reservoir were applied onto Lanes 3, 4, 5, and 6. Samples taken at 0, 10, 20, and 40 minutes respectively from the second sample reservoir were applied onto Lanes 7, 8, 9, and 10. Separation conditions: anolyte: 2 L 2 mM 5-aminocaproic acid adjusted to pH 4.8 with HCl, also containing 5 mM NaCl, catholyte: 2 L 2 mM MOPSO adjusted to pH 6.8 with NaOH, also containing 5 mM NaCl, sample: 10 mL human plasma sample diluted 1 to 3 with deionized water, separation time: 40 minutes, applied potential: 250 V, first ion-permeable barrier between the first electrolyte chamber and the first sample chamber: polyacrylamide membrane with a nominal molecular mass cut-off of 150,000 dalton, second ion-permeable barrier between the first sample chamber and the second sample chamber: pI=5.8 isoelectric membrane, third ion-permeable barrier between the second sample chamber and the second electrolyte chamber: polyacrylamide membrane with a nominal molecular mass cut-off of 150,000 dalton.

FIG. 14 shows the image of an SDS-PAGE gel used to analyze the protein bands present in the aliquots collected from the first and second sample reservoirs of the electrophoretic apparatus during the isolation of IgG from human plasma. Molecular weight markers (Sigma, St. Louis, Mo., USA) were applied onto Lane 1, a pharmaceutical-grade IgG preparation used as reference material onto Lane 2. Samples taken at 0, 10, 20, and 40 minutes respectively from the first sample reservoir were applied onto Lanes 3, 4, 5, and 6. Samples taken at 0, 10, 20, and 40 minutes respectively from the second sample reservoir were applied onto Lanes 7, 8, 9, and 10. IgG was purified within 40 minutes.

These examples indicate that remarkably rapid separation of ampholytic components can be achieved using the apparatus and method disclosed here. The high production rates are attributed to the short electrophoretic migration distances, high electric field strength and good heat dissipation characteristics of the system.

The invention has been described herein by way of example only. It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive. Other features and aspects of this invention will be appreciated by those skilled in the art upon reading and comprehending this disclosure. Such features, aspects, and expected variations and modifications of the reported results and examples are clearly within the scope of the invention where the invention is limited solely by the scope of the following claims.

What we claim is:

1. An electrophoretic apparatus comprising:
    a first electrolyte chamber containing a first electrode;
    a second electrolyte chamber containing a second electrode, wherein the second electrolyte chamber is disposed relative to the first electrolyte chamber so that the electrodes are adapted to generate an electric field in an electric field area upon application of a selected electric potential between the electrodes;

a first sample chamber disposed between the first and second electrolyte chambers and proximate to the first electrolyte chamber so as to be at least partially disposed in the electric field area;

a second sample chamber disposed between the first sample chamber and the second electrolyte chamber so as to be at least partially disposed in the electric field area;

a first ion-permeable barrier separating the first and second sample chambers so as to impede convective mixing of the contents in each of the first and second sample chambers;

a second ion-permeable barrier separating the first electrolyte chamber and the first sample chamber so as to impede convective mixing of the contents in each of the first sample chamber and the first electrolyte chamber;

a third ion-permeable barrier separating the second electrolyte chamber and the second sample chamber so as to impede convective mixing of the contents in each of the second sample chamber and the second electrolyte chamber, wherein at least one of the second ion-permeable barrier and the third ion-permeable barrier is an isoelectric membrane;

a first electrolyte reservoir and a second electrolyte reservoir in fluid communication with the first and second electrolyte chambers, respectively;

a first sample reservoir and a second sample reservoir in fluid communication with the first and second sample chambers, respectively, wherein the first sample reservoir is not in fluid communication with the second reservoir;

means adapted for communicating an associated first electrolyte between the first electrolyte chamber and the first electrolyte reservoir;

means adapted for communicating an associated second electrolyte between the second electrolyte chamber and the second electrolyte reservoir;

means adapted for communicating a first fluid between the first sample chamber and the first sample reservoir; and means adapted for communicating a second fluid between the second sample chamber and the second sample reservoir, wherein at least one of the first and second fluid contains at least a sample, wherein application of the selected electric potential cause migration of at least one component through at least one of the ion-permeable barriers.

2. The apparatus according to claim 1 further comprising means adapted for circulating electrolyte from each of the first and second electrolyte reservoirs through the first and second electrolyte chambers forming first and second electrolyte streams; and means adapted for circulating the contents from each of first and second sample reservoirs through the respective first and second sample chambers forming first and second sample streams.

3. The apparatus according to claim 2 wherein the means adapted for communicating the first electrolyte, the second electrolyte, the first fluid, and the second fluid comprise pumping means which are separately controlled for independent movement of the respective fluids.

4. The apparatus according to claim 1 further comprising means adapted for at least one of removing contents from and replacing contents in at least one of the first and second sample reservoirs.

5. The apparatus according to claim 1 further comprising means adapted to maintain the temperature of the first electrolyte, second electrolyte, contents of the first sample chamber, and contents of the second sample chamber.

6. The apparatus according to claim 1 wherein the first electrolyte chamber, second electrolyte chamber, first sample chamber, and second sample chamber are contained in a separation unit wherein the separation unit is selected from the group consisting of a cassette and a cartridge and such separation unit is fluidly connected to the electrolyte reservoirs and the sample reservoirs.

7. The apparatus according to claim 1 wherein the first sample chamber, the second sample chamber and the ion-permeable barriers are provided as an electrophoretic separation unit adapted to be removably positioned between the a first electrolyte chamber the second electrolyte chamber of the electrophoretic apparatus.

8. The apparatus according to claim 1 wherein the first ion-permeable barrier is an isoelectric membrane having a characteristic pI value.

9. An electrophoretic apparatus comprising:

a first electrolyte chamber containing a first electrode;

a second electrolyte chamber containing a second electrode, wherein the second electrolyte chamber is disposed relative to the first electrolyte chamber so that the electrodes are adapted to generate an electric field in an electric field area upon application of a selected electric potential between the electrodes;

a first sample chamber disposed between the first and second electrolyte chambers and proximate to the first electrolyte chamber so as to be at least partially disposed in the electric field area;

a second sample chamber disposed between the first sample chamber and the second electrolyte chamber so as to be at least partially disposed in the electric field area;

a first ion-permeable barrier separating the first and second sample chambers so as to impede convective mixing of the contents in each of the first and second sample chambers;

a second ion-permeable barrier separating the first electrolyte chamber and the first sample chamber so as to impede convective mixing of the contents in each of the first sample chamber and the first electrolyte chamber;

a third ion-permeable barrier separating the second electrolyte chamber and the second sample chamber so as to impede convective mixing of the contents in each of the second sample chamber and the second electrolyte chamber, wherein both the second ion-permeable barrier and the third ion-permeable barrier are isoelectric membranes;

a first electrolyte reservoir and a second electrolyte reservoir in fluid communication with the first and second electrolyte chambers, respectively;

a first sample reservoir and a second sample reservoir in fluid communication with the first and second sample chambers, respectively, wherein the first sample reservoir is not in fluid communication with the second sample reservoir;

means adapted for communicating an associated first electrolyte between the first electrolyte chamber and the first electrolyte reservoir;

means adapted for communicating an associated second electrolyte between the second electrolyte chamber and the second electrolyte reservoir;

means adapted for communicating a first fluid between the first sample chamber and the first sample reservoir; and means adapted for communicating a second fluid between the second sample chamber and the second sample reservoir, wherein at least one of the first and second fluid contains at least a sample, wherein application of the selected electric potential causes migration of at least one component through at least one of the ion-permeable barriers.

10. The apparatus according to claim 9 wherein each of the isoelectric membranes has a different characteristic pI value.

11. The apparatus according to claim 9 wherein the first ion-permeable barrier is an isoelecric membrane having a characteristic pI value.

12. A method for selectively removing at least one component from a selected sample comprising:

communicating a first electrolyte to a first electrolyte chamber containing a first electrode wherein the first electrolyte chamber is in fluid communication with a first electrolyte reservoir;

communicating a second electrolyte to a second electrolyte chamber containing a second electrode, wherein the second electrolyte chamber is disposed opposite the first electrolyte chamber and wherein the second electrolyte chamber is in fluid communication with a second electrolyte reservoir;

communicating a first fluid to a first sample chamber disposed between the first and second electrolyte chambers and proximate to the first electrolyte chamber, wherein the first sample chamber is in fluid communication with a first sample reservoir;

communicating a second fluid to a second sample chamber disposed between the first sample chamber and the second electrolyte chamber, wherein the second sample chamber is in fluid communication with a second sample reservoir, wherein a first ion-permeable barrier separates the first and second sample chambers, a second ion-permeable barrier separates the first electrolyte chamber and the first sample chamber, and a third ion-permeable barrier separates the second sample chamber and the second electrolyte chamber, wherein the ion-permeable barriers impede convective mixing between the respective chambers, wherein at least one of the second ion-permeable barrier and the third ion-permeable barrier is an isoelectric membrane, wherein at least one of the first and second fluids contains at least a sample; and applying a selected electric potential to cause migration of at least one selected component through at least one of the ion-permeable barriers.

13. The method according to claim 12 further comprising removing at least one component from at least one of the first and second sample reservoirs.

14. The method according to claim 12 further comprising replacing the components in at least one of the first and second sample reservoirs.

15. The method according to claim 12 wherein substantially all trans-barrier migration of the components is initiated upon the application of the selected electric potential.

16. The method according to claim 12 wherein the application of the selected electric potential is maintained until at least one desired component reaches the desired purity in at least one of the first and second sample chambers.

17. A method for selectively removing at least one component from a selected sample comprising:

communicating a first electrolyte to a first electrolyte chamber containing a first electrode wherein the first electrolyte chamber is in fluid communication with a first electrolyte reservoir;

communicating a second electrolyte to a second electrolyte chamber containing a second electrode, wherein the second electrolyte chamber is disposed opposite the first electrolyte chamber and wherein the second electrolyte chamber is in fluid communication with a second electrolyte reservoir;

communicating a first fluid to a first sample chamber disposed between the first and second electrolyte chambers and proximate to the first electrolyte chamber, wherein the first sample chamber is in fluid communication with a first sample reservoir;

communicating a second fluid to a second sample chamber disposed between the first sample chamber and the second electrolyte chamber, wherein the second sample chamber is in fluid communication with a second sample reservoir, wherein a first ion-permeable barrier separates the first and second sample chambers, a second ion-permeable barrier separates the first electrolyte chamber and the first sample chamber, and a third ion-permeable barrier separates the second sample chamber and the second electrolyte chamber, wherein the ion-permeable barriers impede convective mixing between the respective chambers, wherein both the second ion-permeable barrier and the third ion-permeable barrier are isoelectric membranes, wherein at least one of the first and second fluids contains at least a sample; and applying a selected electric potential to cause migration of at least one selected component through at least one of the ion-permeable barriers.

18. An electrophoretic separation unit comprising:

a first electrolyte chamber containing a first electrode;

a second electrolyte chamber containing a second electrode, wherein the second electrolyte chamber is disposed relative to the first electrolyte chamber so that the electrodes are adapted to generate an electric field in an electric field area upon application of a selected electric potential between the electrodes;

a first sample chamber disposed between the first and second electrolyte chambers and proximate to the first electrolyte chamber so as to be at least partially disposed in the electric field area;

a second sample chamber disposed between the first sample chamber and the second electrolyte chamber so as to be at least partially disposed in the electric field area;

an isoelectric barrier separating the first and second sample chambers so as to impede convective mixing of the contents in each of the first and second sample chambers;

a first ion-permeable barrier separating the first electrolyte chamber and the first sample chamber so as to impede convective mixing of the contents in each of the first sample chamber and the first electrolyte chamber;

a second ion-permeable barrier separating the second electrolyte chamber and the second sample chamber so as to impede convective mixing of the contents in each of the second sample chamber and second electrolyte chamber;

means adapted for communicating an associated first electrolyte to the first electrolyte chamber;

means adapted for communicating an associated second electrolyte to the second electrolyte chamber;

means adapted for communicating a first fluid to the first sample chamber; and means adapted for communicating a second fluid to the second sample chamber, wherein the means adapted for communicating a first fluid and the means adapted for communicatng the second fluid are not in fluid communication with each other, wherein at least one of the first and second fluids contains at least a sample, wherein application of the selected electric potential causes migration of at least one component through at least one of the ion-permeable barriers, wherein at least one of the first ion-permeable barrier and the second ion-permeable barrier is an isoelectric membrane.

19. An electrophoretic separation unit comprising:

a first electrolyte chamber containing a first electrode;

a second electrolyte chamber containing a second electrode, wherein the second electrolyte chamber is disposed relative to the first electrolyte chamber so that the electrodes are adapted to generate an electric field in an electric field area upon application of a selected electric potential between the electrodes;

a first sample chamber disposed between the first and second electrolyte chambers and proximate to the first electrolyte chamber so as to be at least partially disposed in the electric field area;

a second sample chamber disposed between the first sample chamber and the second electrolyte chamber so as to be at least partially disposed in the electric field area;

an isoelectric barrier separating the first and second sample chambers so as to impede convective mixing of the contents in each of the first and second sample chambers;

a first ion-permeable barrier separating the first electrolyte chamber and the first sample chamber so as to impede convective mixing of the contents in each of the first sample chamber and the first electrolyte chamber;

a second ion-permeable barrier separating the second electrolyte chamber and the second sample chamber so as to impede convective mixing of the contents in each of the second sample chamber and second electrolyte chamber, wherein both the first ion-permeable barrier and the second ion-permeable barrier are isoelectric membranes;

means adapted for communicating an associated first electrolyte to the first electrolyte chamber;

means adapted for communicating an associated second electrolyte to the second electrolyte chamber;

means adapted for communicating a first fluid to the first sample chamber; and means adapted for communicating a second fluid to the second sample chamber, wherein the means adapted for communicating a first fluid and the means adapted for communicating the second fluid are not in fluid communication with each other, wherein at least one of the first and second fluids contains at least a sample, wherein application of the selected electric potential causes migration of at least one component through at least one of the ion-permeable barriers.

20. A method for selectively removing at least one component from a selected sample comprising:

communicating a first electrolyte to a first electrolyte chamber containing a first electrode;

communicating a second electrolyte to a second electrolyte chamber containing a second electrode;

communicating a first fluid to a first sample chamber disposed between the first and second electrolyte chambers and proximate to the first electrolyte chamber;

communicating a second fluid to a second sample chamber disposed between the first sample chamber and the second electrolyte chamber, wherein an isoelectric barrier separates the first and second sample chambers, a first ion-permeable barrier separates the first electrolyte chamber and the first sample chamber, and a second ion-permeable barrier separates the second sample chamber and the second electrolyte chamber, wherein the barriers impede convective mixing between the respective chambers, wherein at least one of the first ion permeable barrier and the second ion permeable barrier is an isoelectric membrane, wherein at least one of the first and second fluids contains a sample; and applying a selected electric potential to cause migration of at least one selected component though at least one of the barriers.

21. The method according to claim 20 wherein at least one of the components in the first and second sample chambers has a pI value.

22. The method according to claim 20 wherein the isoelectric barrier is an isoelectric membrane.

23. The method according to claim 20 wherein one of the first ion-permeable barrier and the second ion-permeable barrier is a membrane having characteristic average pore size and pore size distribution.

24. A method for selectively removing at least one component from a selected sample comprising:

communicating a first electrolyte to a first electrolyte chamber containing a first electrode;

communicating a second electrolyte to a second electrolyte chamber containing a second electrode;

communicating a first fluid to a first sample chamber disposed between the first and second electrolyte chambers and proximate to the first electrolyte chamber;

communicating a second fluid to a second sample chamber disposed between the first sample chamber and the second electrolyte chamber, wherein an isoelectric barrier separates the first and second sample chambers, a first ion-permeable barrier separates the first electrolyte chamber and the first sample chamber, and a second ion-permeable barrier separates the second sample chamber and the second electrolyte chamber, wherein the barriers impede convective mixing between the respective chambers, wherein both the first ion-permeable barrier and the second ion-permeable barrier are isoelectric membranes, wherein at least one of the first and second fluids contains a sample; and applying a selected electric potential to cause migration of at least one selected component though at least one of the barriers.

25. The method according to claim 24 wherein each of the isoelectric membranes has a different characteristic pI value.

26. The method according to claim 24 wherein substantially all trans-barrier migration of the components is initiated upon the application of the selected electric potential.

27. An electrophoretic apparatus comprising:

a first electrolyte chamber containing a first electrode;

a second electrolyte chamber containing a second electrode, wherein the second electrolyte chamber is disposed relative to the first electrolyte chamber so that the electrodes are adapted to generate an electric field in an electric field area upon application of a selected electric potential between the electrodes;

a first sample chamber disposed between the first and second electrolyte chambers and proximate to the first electrolyte chamber so as to be at least partially disposed in the electric field area;

a second sample chamber disposed between the first sample chamber and the second electrolyte chamber so as to be at least partially disposed in the electric field area;

a first isoelectric barrier having a characteristic pI separating the first and second sample chambers so as to impede convective mixing of the contents in each of the first and second sample chambers;

a second isoelectric barrier having a characteristic pI separating the first electrolyte chamber and the first sample chamber so as to impede convective mixing of the contents in each of the first sample chamber and the first electrolyte chamber;

a membrane having a characteristic average pore size and pore size distribution separating the second sample chamber and the second electrolyte chamber so as to impede convective mixing of the contents in each of the second sample chamber and the second electrolyte chamber;

a first electrolyte reservoir and a second electrolyte reservoir in fluid communication with the first and second electrolyte chambers, respectively;

a first sample reservoir and a second sample reservoir in fluid communication with the first and second sample chambers, respectively;

means adapted for communicating an associated first electrolyte between the first electrolyte chamber and the first electrolyte reservoir;

means adapted for communicating an associated second electrolyte between the second electrolyte chamber and the second electrolyte reservoir;

means adapted for communicating a first fluid between the first sample chamber and the first sample reservoir; and means adapted for communicating a second fluid between the second sample chamber and the second sample reservoir, wherein at least one of the first and second fluids contains at least a sample;

wherein application of the selected electric potential causes migration of at least one component through at least one of the barriers.

28. An electrophoretic apparatus comprising:

a first electrolyte chamber containing a first electrode;

a second electrolyte chamber containing a second electrode, wherein the second electrolyte chamber is disposed relative to the first electrolyte chamber so that the electrodes are adapted to generate an electric field in an electric field area upon application of a selected electric potential between the electrodes;

a first sample chamber disposed between the first and second electrolyte chambers and proximate to the first electrolyte chamber so as to be at least partially disposed in the electric field area;

a second sample chamber disposed between the first sample chamber and the second electrolyte chamber so as to be at least partially disposed in the electric field area;

a first isoelectric barrier having a characteristic pI separating the first and second sample chambers so as to impede convective mixing of the contents in each of the first and second sample chambers;

a second isoelectric barrier having a characteristic pI separating the first electrolyte chamber and the first sample chamber so as to impede convective mixing of the contents in each of the first sample chamber and the first electrolyte chamber;

a third isoelectric barrier having a characteristic pI separating the second electrolyte chamber and the second sample chamber so as to impede convective mixing of the contents in each of the second sample chamber and second electrolyte chamber;

a first electrolyte reservoir and a second electrolyte reservoir in fluid communication with the first and second electrolyte chambers, respectively;

a first sample reservoir and a second sample reservoir in fluid communication with the first and second sample chambers, respectively;

means adapted for communicating an associated first electrolyte between the first electrolyte chamber and the first electrolyte reservoir;

means adapted for communicating an associated second electrolyte between the second electrolyte chamber and the second electrolyte reservoir;

means adapted for communicating a first fluid between the first sample chamber and the first sample reservoir; and means adapted for communicating a second fluid between the second sample chamber and the second sample reservoir, wherein at least one of the first and second fluids contains at least a sample, wherein upon application of the selected electric potential causes migration of at least one component through at least one of the barriers.

* * * * *